(12) United States Patent
He et al.

(10) Patent No.: US 10,100,143 B2
(45) Date of Patent: Oct. 16, 2018

(54) DIHYDROPYRROLO[2,3-F]INDOLE-DIKETOPYRROLOPYRROLE SEMICONDUCTING MATERIALS, AND METHODS AND USES THEREOF

(71) Applicant: Corning Incorporated, Corning, NY (US)

(72) Inventors: Mingqian He, Horseheads, NY (US); Jieyu Hu, Littleton, CO (US); Adama Tandia, Nelson, PA (US); Weijun Nui, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 15/248,197

(22) Filed: Aug. 26, 2016

(65) Prior Publication Data

US 2016/0362517 A1 Dec. 15, 2016

Related U.S. Application Data

(63) Continuation of application No. PCT/US2015/017710, filed on Feb. 26, 2015.

(Continued)

(51) Int. Cl.
*C08G 73/06* (2006.01)
*C08G 61/00* (2006.01)
(Continued)

(52) U.S. Cl.
CPC ......... *C08G 61/126* (2013.01); *C07D 519/00* (2013.01); *C08G 61/124* (2013.01); *H01L 51/0036* (2013.01); *H01L 51/0043* (2013.01); *H01L 51/0068* (2013.01); *H01L 51/0072* (2013.01); *C08G 2261/124* (2013.01); *C08G 2261/18* (2013.01); *C08G 2261/3223* (2013.01); *C08G 2261/3241* (2013.01); *C08G 2261/3243* (2013.01); *C08G 2261/334* (2013.01); *C08G 2261/344* (2013.01); *C08G 2261/414* (2013.01); *C08G 2261/51* (2013.01);
(Continued)

(58) Field of Classification Search
CPC ...................................................... C08G 73/06
USPC ...................................................... 528/367
See application file for complete search history.

(56) References Cited

U.S. PATENT DOCUMENTS 8,217,183 B2   7/2012   He et al.
8,278,346 B2   10/2012  He et al.
(Continued)

FOREIGN PATENT DOCUMENTS

CN     102834945 A      12/2012
WO     WO 2013135339 A2   9/2013

OTHER PUBLICATIONS

Grant & Hackh's Chemical Dictionary (5th Ed 1987) definition of 'Compound', p. 148.
(Continued)

*Primary Examiner* — Duc Truong
(74) *Attorney, Agent, or Firm* — Shantanu Pathak; Jason A Barron

(57) ABSTRACT

Described herein are heterocyclic organic compounds. More specifically, described herein are compounds based on the combination of fused pyrrole structures with diketopyrrolopyrrole structures, methods for making these compounds, and uses thereof. The compounds disclosed have improved electronic, polymerization and stability properties that allow for improved material processability and inclusion in organic semiconductor devices.

20 Claims, 1 Drawing Sheet

Related U.S. Application Data

(60) Provisional application No. 61/946,004, filed on Feb. 28, 2014.

(51) Int. Cl.
  *C07D 519/00* (2006.01)
  *C08G 61/12* (2006.01)
  *H01L 51/00* (2006.01)
  *H01L 51/05* (2006.01)
  *H01L 51/50* (2006.01)

(52) U.S. Cl.
  CPC ..... *C08G 2261/91* (2013.01); *C08G 2261/92* (2013.01); *H01L 51/0558* (2013.01); *H01L 51/5012* (2013.01)

(56) References Cited

U.S. PATENT DOCUMENTS

| | | |
|---|---|---|
| 9,062,152 B2 | 6/2015 | Grenier |
| 9,166,167 B2 | 10/2015 | Chen et al. |
| 2011/0004004 A1 | 1/2011 | Hao et al. |
| 2011/0031762 A1 | 1/2011 | Thomas et al. |
| 2011/0240973 A1 | 10/2011 | Dueggeli et al. |
| 2011/0317628 A1 | 12/2011 | Lee et al. |
| 2012/0071617 A1 | 3/2012 | Dueggeli et al. |
| 2012/0161117 A1 | 6/2012 | Chen et al. |
| 2013/0085256 A1 | 4/2013 | He et al. |
| 2013/0264552 A1 | 10/2013 | Cui et al. |
| 2015/0045560 A1 | 2/2015 | He et al. |

OTHER PUBLICATIONS

Gruhn et al., "Hole- and Electron-Vibrational Couplings in Oligoacene Crystals: Intramolecular Contributions", 89 Phys. Rev.Lett. 275503 (2002).

Matthews et al., "Scalable Synthesis of Fused Thiophene-Diketopyrrolopyrrole Semiconducting Polymers Processed from Nonchlorinated Solvents into High Performance Thin Film Transistors", Chem. Mater. 2013, 25, pp. 782.

Zhou et al., "Diketopyrrolopyrrole-Based Semiconducting Polymer for Photovoltaic Device with Photocurrent Response Wavelengths up to 1.1 um", Macromolecules 2010 , 43, pp. 821-826.

Marcus et al., "Electron transfer reactions in chemistry. Theory and experiment", 65 Rev. Mod. Phys. 599-610 (1993).

Loser et al., "A Naphthodithiophene-Diketopyrrolopyrrole Donor Molecule for Efficient Solution-Processed Solar Cells", Journal of the American Chemical Society, 2011, 133, pp. 8142-8145.

Malagoli et al., "Density functional theory study of the geometric structure and energetics of triphenylamine-based hole-transporting molecules", Chemical Physics Letters, 327, 2000, pp. 13-17.

Nielsen et al., "Recent Advances in the Development of Semiconducting DPP-Containing Polymers for Transistor Applications",Adv. Mater. 2013, 25, pp. 1859-1880.

Tieke et al., "Conjugated polymers containing diketopyrrolopyrrole units in the main chain 11", Beilstein Journal of Organic Chemistry, vol. 6, Aug. 31, 2010, pp. 830-845.

Li et al., "A stable solution-processed polymer semiconductor with record high-mobility for printed transistors", Scientific Reports, 2012; 2, pp. 1-9.

Nguyen et al., "Synthesis and Polymerization of Fused-Ring Thienodipyrrole Monomers", Macromolecular Chemistry and Physics, 2012, 213, 425-430.

Cai et al., "Extended Conjugated Donor-Acceptor Molecules with E-(1,2 Difluorovinyl) and Diketopyrrolopyrrole (DPP) Moieties toward High-Performance Ambipolar Organic Semiconductors", Chemistry—An Asian Journal, vol. 9 , No. 4, Jan. 23, 2014, pp. 1068-1075.

PCT/US2015/017710 International Search Report and Written Opinion of the ISA; dated May 12, 2015; p. 1-12; EPO.

Li et al., "Alkyl Side Chain Impact on the Charge Transport and Photovoltaic Properties of Benzodithiophene and Diketopyrrolopyrrole-Based Copolymers", The Journal of Physical Chemistry C, 2011 , 115 , pp. 18002-18009.

Dou et al., "Tandem polymer solar cells featuring a spectrally matched low-bandgap polymer", Nature Photonics, 2012, 6, pp. 180-185.

Kanimozhi et al., "Synthesis of Diketopyrrolopyrrole Containing Copolymers: A Study of Their Optical and Photovoltaic Properties", J. Phys. Chem. B.; 2010 , 114 , pp. 3095-3103.

Yuan et al., "Benzo[2,1-b;3,4-b']dithiophene-Based Low-Bandgap Polymers for Photovoltaic Applications", Journal of Polymer Science, Part A: Polym. Chem. 2011 , 49 , pp. 701-711.

Zhang et al., "Synthesis and Characterization of Dioctyloxybenzol[1,2-b:4,3-b']-dithiophene-Containing Copolymers for Polymer Solar Cells", Macromolecules, ACS Publications—American Chemical Society, pp. 7625-7631.

Zoombelt et al., "Small Band Gap Polymers Based on Diketopyrrolopyrrole", J. Mater. Chem, 2010, 20, pp. 2240-2246.

Nelson et al., "Transistor Paint: High Mobilities in Small Bandgap Polymer Semiconductor Based on the STrong Acceptor, Diketopyrrolopyrrole and Strong Donor, Dithienopyrrole", Advanced Materials 2010 , 22 , pp. 4617-4621.

Patil et al., "Synthesis and photovoltaic properties of narrow band gap copolymers of dithieno[3,2-b:2',3'-d]thiophene and diketopyrrolopyrrole", Polymer Chemistry, 2011 , 2 , pp. 2907-2916.

Liu et al., "Effects of Heteroatom Substitutions on the Crystal Structure, Film Formation, and Optoelectronic Properties of Diketopyrrolopyrrole-Based Materials", Advanced Functional Materials, 2013, 23, pp. 47-56.

Niebel et al; "Dibenzo [2,3:5,6] Pyrrolizino [1,7-BC] Indolo [1,2,3-LM] Carbazole: A New Electron Donor"; 34 New J. Chem. 1243-1246 (2010).

Samsoniya et al; "Synthesis and Antimicrobial Activity of a Number of Pyrrolo Indole Derivatives"; Pharmaceutical Chemistry Journal, vol. 45, No. 1, Apr. 2011, p. 22-25.

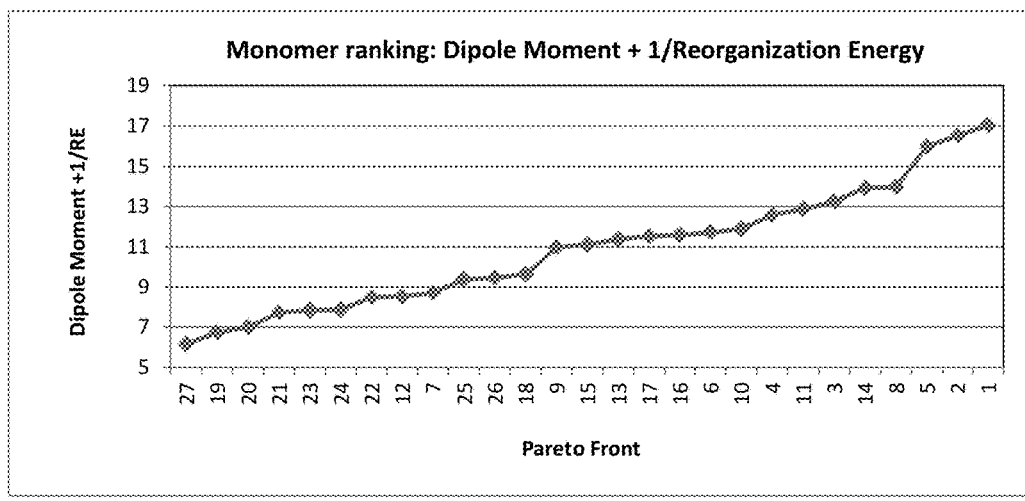

DIHYDROPYRROLO[2,3-F]INDOLE-DIKETOPYRROLOPYRROLE SEMICONDUCTING MATERIALS, AND METHODS AND USES THEREOF

This application is a continuation of International Application No. PCT/US15/17710 filed Feb. 26, 2015, the content of which claims the benefit of priority under 35 U.S.C. § 119 of U.S. Provisional Application Ser. No. 61/946,004, filed on Feb. 28, 2014, the content of which is relied upon and incorporated herein by reference in its entirety.

FIELD

Described herein are compositions including heterocyclic organic compounds. More specifically, described herein are fused pyrrole-containing compounds in combination with diketopyrrolopyrrole compounds, methods for making them, and uses thereof.

TECHNICAL BACKGROUND

Highly conjugated organic materials, due to their interesting electronic and optoelectronic properties, are being investigated for use in a variety of applications, including organic semiconductors (OSCs), field effect transistors (FETs), thin-film transistors (TFTs), organic light-emitting diodes (OLEDs), electro-optic (EO) applications, as conductive materials, as two photon mixing materials, as organic semiconductors, and as non-linear optical (NLO) materials.

In particular, OSCs have attracted a great amount of attention in the research community due to their advantages over inorganic semiconductors, including easy processing, high mechanical flexibility, low cost production, and low weights. Polycyclic aromatic compounds, such as oligothiophenes, acenes, rylenes, phthalocyanens, and polythiophene, have been widely studied as semiconductor materials.

Among the organic p-type semiconductors, pentacene exhibits charge mobilities well above 1 cm²/V·s in organic field effect transistor devices. This number has been set up as a bench mark for new small molecule systems in terms of mobility requirements. However, due to the continuing need for improved performance and stability in semiconductor structures, there continues to be an unmet need to develop better performing OSCs that have improved mobility, are structurally stable, and applicable to the large number of potential applications seen in the various high technology markets.

SUMMARY

Embodiments comprise a rationally designed family of compounds and polymers comprising optionally-substituted dihydropyrroloindoles ("DHPI"), dipyrrolothiophenes or fused pyrroles (all generally referred to as "pyrrole groups" herein) bridged to optionally substituted diketopyrrolopyrroles ("DPP"). The materials have advantages over DPP alone in that they are soluble in non-chlorinated solvents, efficiently synthesized, and show very high mobilities in non-chlorinated solvents. Further, the compounds are relatively easy to modify and substituents can be introduced to multiple positions which allows for fine tuning material packing behaviors.

A first embodiment comprises a compound of formula:

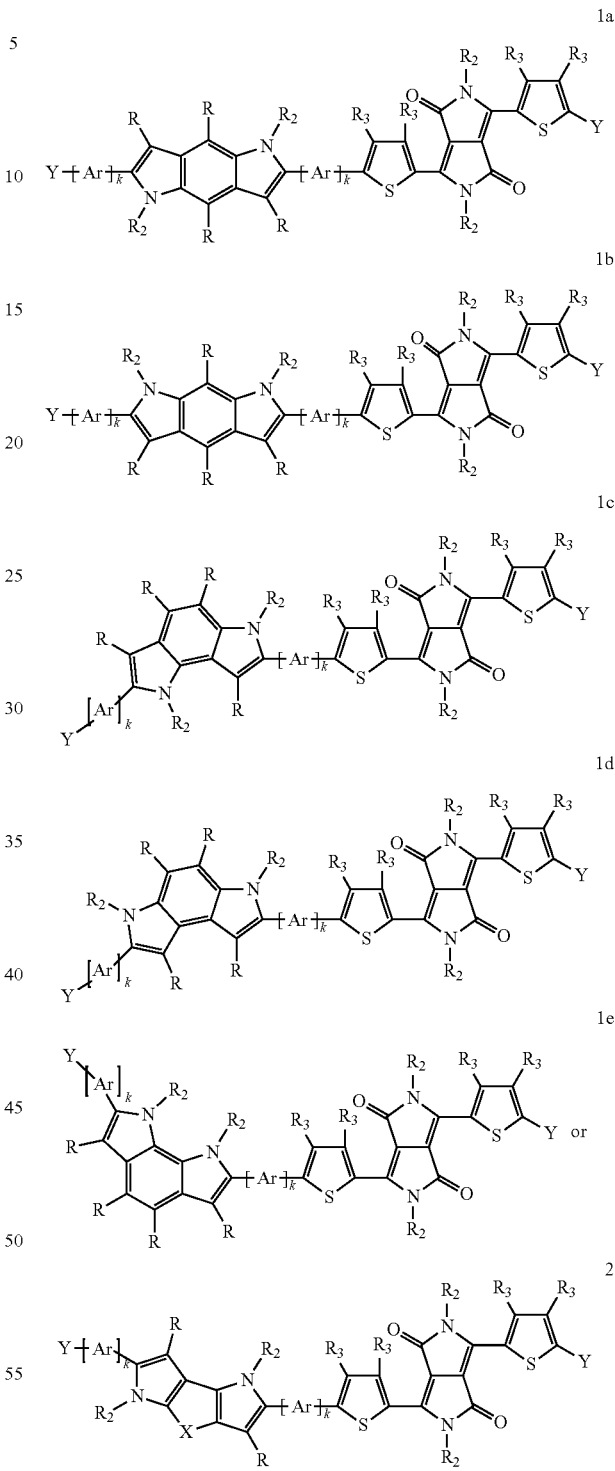

wherein Ar is an optionally substituted aromatic or heteroaromatic group; k is an integer from 0 to 5 with the proviso that when k is 0, the structure results in a direct bond between the thiophene and pyrrole group; each X is independently $NR_1$, $PR_1$, $AsR_1$, Sb, O, S, Te, or Se, with the proviso that due to conjugation, X may be bonded to one or more additional $R_1$; each Y is independently H, halo, trialkylsilane, optionally substituted $C_1$-$C_{40}$ alkyl, optionally substituted aralkyl, alkoxy, alkylthio, optionally substituted $C_2$-$C_{40}$ alkenyl, optionally substituted $C_2$-$C_{40}$ alkynyl, aminocarbonyl, acylamino, acyloxy, aryl, aryloxy, optionally substituted amino, carboxyalkyl, optionally substituted cycloalkyl, optionally substituted cycloalkenyl, halo, acyl, optionally substituted heteroaryl, optionally substituted heteroaralkyl, heteroaryloxy, optionally substituted heterocyclyl, thiol, alkylthio, heteroarylthiol, optionally substituted sulfoxide, optionally substituted sulfone, OSO-alkyl, Mg-halo, Zn-halo, Sn(alkyl)$_3$, SnH$_3$, B(OH)$_2$, B(alkoxy)$_2$, or OTs; and each R, $R_1$, $R_2$, and $R_3$ is independently H, halo, optionally substituted $C_1$-$C_{40}$ alkyl, optionally substituted aralkyl, alkoxy, alkylthio, optionally substituted $C_2$-$C_{40}$ alkenyl, optionally substituted $C_2$-$C_{40}$ alkynyl, aminocarbonyl, acylamino, acyloxy, optionally substituted aryl, aryloxy, optionally substituted amino, carboxyalkyl, optionally substituted cycloalkyl, optionally substituted cycloalkenyl, halo, acyl, optionally substituted hetero aryl, optionally substituted heteroaralkyl, heteroaryloxy, optionally substituted heterocyclyl, thiol, alkylthio, heteroarylthiol, optionally substituted sulfoxide, or optionally substituted sulfone.

In some embodiments, the compound comprises 1a or 1b. In other embodiments, the compound comprises 1c, 1d, or 1e. In still other embodiments, the compound comprises 2. In some embodiments, X is $NR_1$, $PR_1$, $AsR_1$, Sb, O, S, Se, or Te; and each R, $R_1$, $R_2$, and $R_3$ is independently H, halo, optionally substituted $C_1$-$C_{40}$ alkyl, optionally substituted aralkyl, alkoxy, alkylthio, optionally substituted $C_2$-$C_{40}$ alkenyl, optionally substituted $C_2$-$C_{40}$ alkynyl, aminocarbonyl, acylamino, acyloxy, optionally substituted aryl, aryloxy, optionally substituted amino, carboxyalkyl, optionally substituted cycloalkyl, optionally substituted cycloalkenyl, halo, acyl, optionally substituted heteroaryl, optionally substituted heteroaralkyl, heteroaryloxy, optionally substituted heterocyclyl, thiol, alkylthio, heteroarylthiol, optionally substituted sulfoxide, or optionally substituted sulfone.

In other embodiments, each R, $R_1$, $R_2$, and $R_3$ is independently H, halo, optionally substituted $C_1$-$C_{20}$ alkyl, optionally substituted aralkyl, alkoxy, alkylthio, optionally substituted $C_2$-$C_{20}$ alkenyl, optionally substituted $C_2$-$C_{20}$ alkynyl, optionally substituted cycloalkyl, optionally substituted cycloalkenyl, halo, optionally substituted heterocyclyl, or an optionally substituted aryl or optionally substituted heteroaryl from the group consisting of phenyl, thiophenyl, furanyl, pyrrolyl, imidazolyl, triazolyl, oxazolyl, thiazolyl, pyridinyl, pyrimidinyl, triazinyl, naphthalenyl, isoquinolinyl, quinolinyl, or naphthyridinyl. In some embodiments, each $R_2$ is independently H, halo, or optionally substituted $C_1$-$C_{20}$ alkyl.

In particular embodiments, it is advantageous to have at least one or more of R, $R_2$, or $R_3$ independently be an optionally substituted $C_1$-$C_{20}$ alkyl, and in particular an optionally substituted branched $C_1$-$C_{20}$ alkyl. Particular embodiments may have optionally substituted $C_1$-$C_{20}$ alkyl groups only on one or more $R_2$ groups, or alternatively only on one or more R groups.

In some embodiments, the compound comprises 1a, 1b, 1c, 1d, 1e or 2, and the hole reorganization energy is less than 0.75 eV, less than 0.65, less than 0.5, less than 0.4, or less than 0.35 eV. In some embodiments, the hole reorganization energy is from about 0.05 to about 0.75, about 0.05 to about 0.65, about 0.05 to about 0.5, about 0.05 to about 0.04 or about 0.05 to about 0.35 eV.

Another embodiment comprises a polymer of formula:

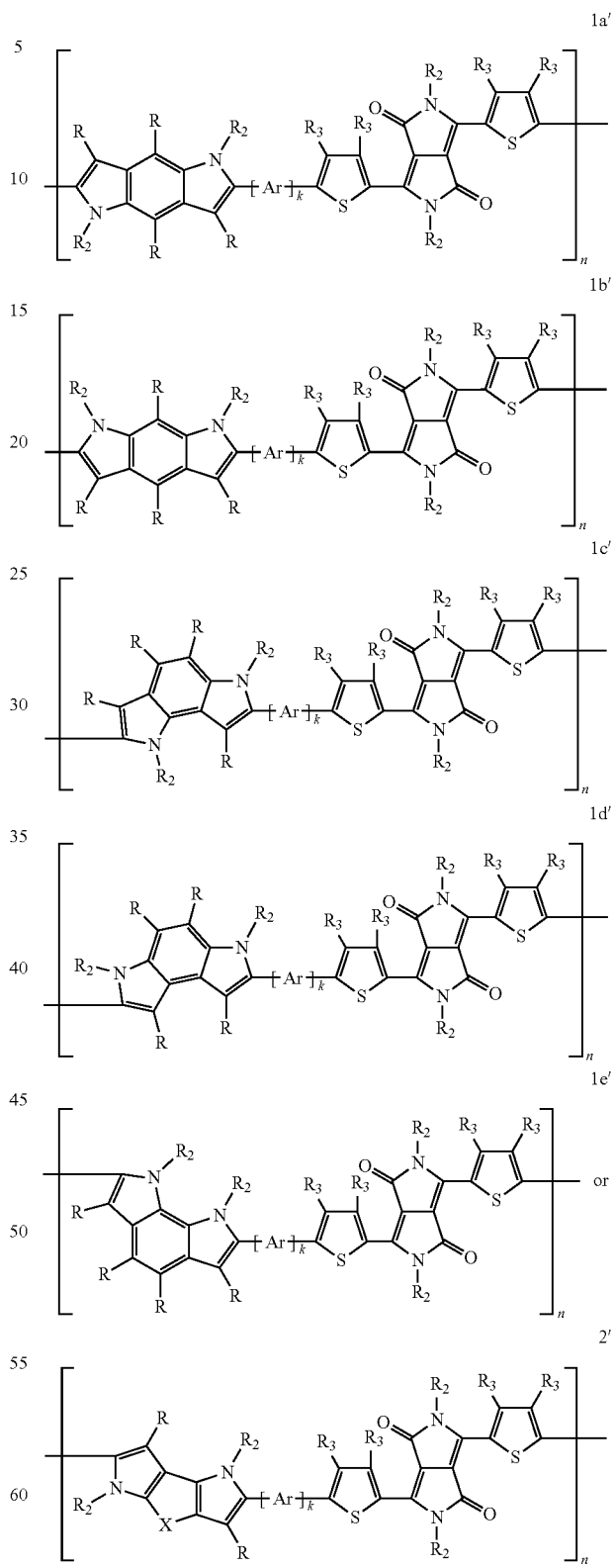

wherein Ar is an optionally substituted aromatic or heteroaromatic group or conjugated group; k is an integer from 0 to 5 with the proviso that when k is 0, the structure results in a direct bond between the thiophene and diindole groups; n is an integer greater than zero; each X is independently $NR_1$, $PR_1$, $AsR_1$, Sb, O, S, Te, or Se, with the proviso that due to conjugation, X may be bonded to one or more additional $R_1$; each R, $R_1$, $R_2$, and $R_3$ is independently H, halo, optionally substituted $C_1$-$C_{40}$ alkyl, optionally substituted aralkyl, alkoxy, alkylthio, optionally substituted $C_2$-$C_{40}$ alkenyl, optionally substituted $C_2$-$C_{40}$ alkynyl, aminocarbonyl, acylamino, acyloxy, optionally substituted aryl, aryloxy, optionally substituted amino, carboxyalkyl, optionally substituted cycloalkyl, optionally substituted cycloalkenyl, acyl, optionally substituted heteroaryl, optionally substituted heteroaralkyl, heteroaryloxy, optionally substituted heterocyclyl, thiol, alkylthio, heteroarylthiol, optionally substituted sulfoxide, or optionally substituted sulfone.

In some embodiments, the compound comprises 1a' or 1b'. In other embodiments, the compound comprises 1c', 1d', or 1e'. In still other embodiments, the compound comprises 2'. In some embodiments, for 1a', 1b', 1c', 1d', 1e', or 2', X is $NR_1$, $PR_1$, $AsR_1$, Sb, O, S, Se, or Te, with the proviso that due to conjugation, $X_1$ may be bonded to one or more additional $R_1$; and each R, $R_1$, $R_2$, and $R_3$ is independently H, halo, optionally substituted $C_1$-$C_{20}$ alkyl, optionally substituted aralkyl, alkoxy, alkylthio, optionally substituted $C_2$-$C_{20}$ alkenyl, optionally substituted $C_2$-$C_{20}$ alkynyl, aminocarbonyl, acylamino, acyloxy, optionally substituted aryl, aryloxy, optionally substituted amino, carboxyalkyl, optionally substituted cycloalkyl, optionally substituted cycloalkenyl, halo, acyl, optionally substituted heteroaryl, optionally substituted heteroaralkyl, heteroaryloxy, optionally substituted heterocyclyl, thiol, alkylthio, heteroarylthiol, optionally substituted sulfoxide, or optionally substituted sulfone.

In other embodiments, each R, $R_1$, $R_2$, and $R_3$ is independently H, halo, optionally substituted $C_1$-$C_{20}$ alkyl, optionally substituted aralkyl, alkoxy, alkylthio, optionally substituted $C_2$-$C_{20}$ alkenyl, optionally substituted $C_2$-$C_{20}$ alkynyl, optionally substituted cycloalkyl, optionally substituted cycloalkenyl, halo, optionally substituted heterocyclyl, or an optionally substituted aryl or optionally substituted heteroaryl from the group consisting of phenyl, thiophenyl, furanyl, pyrrolyl, imidazolyl, triazolyl, oxazolyl, thiazolyl, pyridinyl, pyrimidinyl, triazinyl, naphthalenyl, isoquinolinyl, quinolinyl, or naphthyridinyl. In some embodiments, each $R_2$ is independently H, halo, or optionally substituted $C_1$-$C_{20}$ alkyl.

In particular embodiments, it is advantageous to have at least one or more of R, $R_2$, or $R_3$ independently be an optionally substituted $C_1$-$C_{20}$ alkyl, and in particular an optionally substituted branched $C_1$-$C_{20}$ alkyl. Particular embodiments may have optionally substituted $C_1$-$C_{20}$ alkyl groups only on one or more $R_2$ groups, or alternatively only on one or more R groups.

In some embodiments, for 1a', 1b', 1c', 1d', 1e', or 2', n is an integer from 1 to 500 and k is an integer from 1 to 3.

Another embodiment comprises a method of synthesizing a compound comprising:

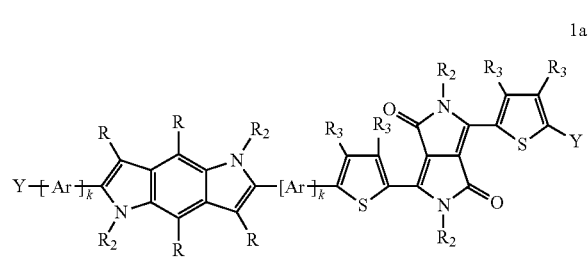

1a

-continued

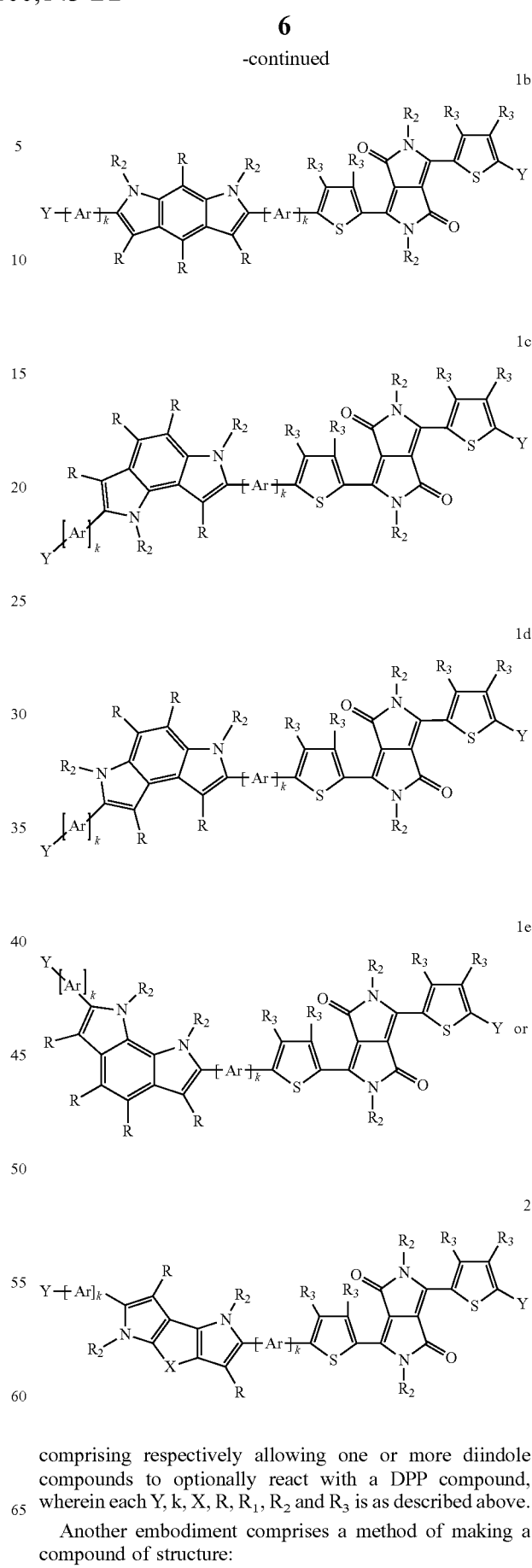

1b

1c

1d

1e

2 comprising respectively allowing one or more diindole compounds to optionally react with a DPP compound, wherein each Y, k, X, R, $R_1$, $R_2$ and $R_3$ is as described above.

Another embodiment comprises a method of making a compound of structure:

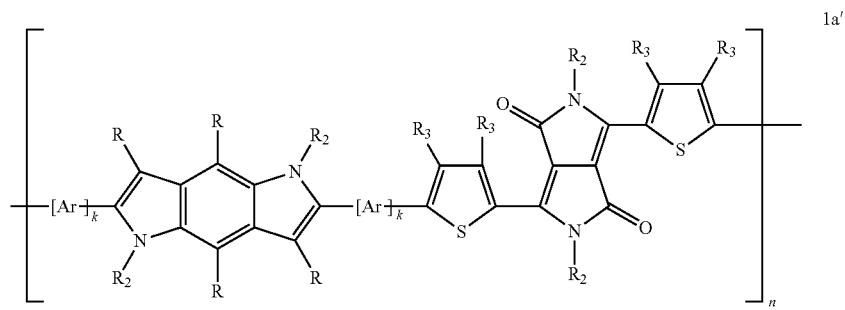
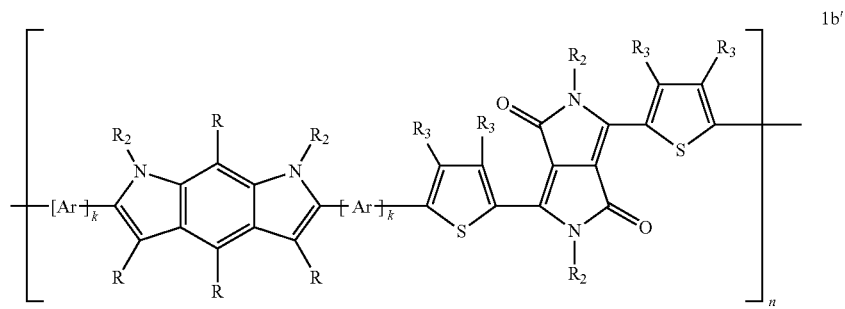
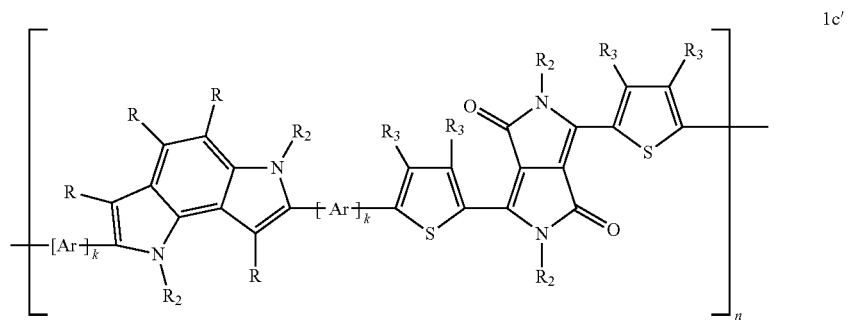
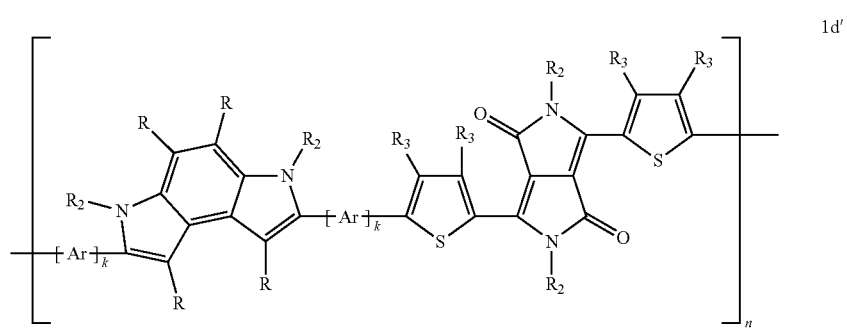
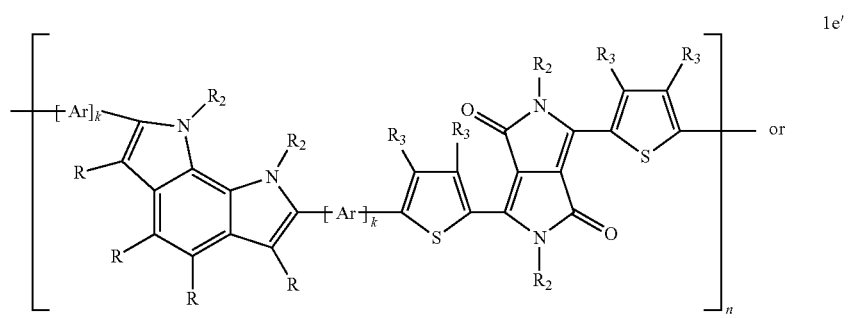

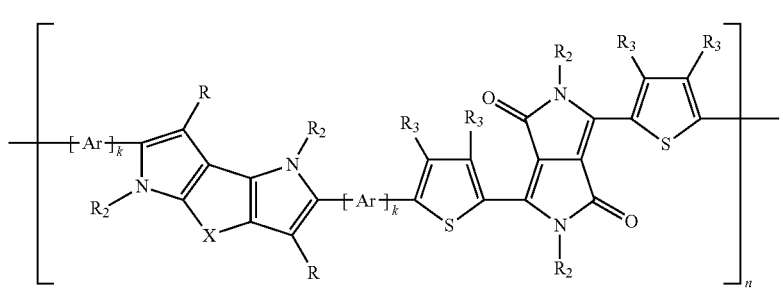

Comprising respectively polymerizing a compound of structure:

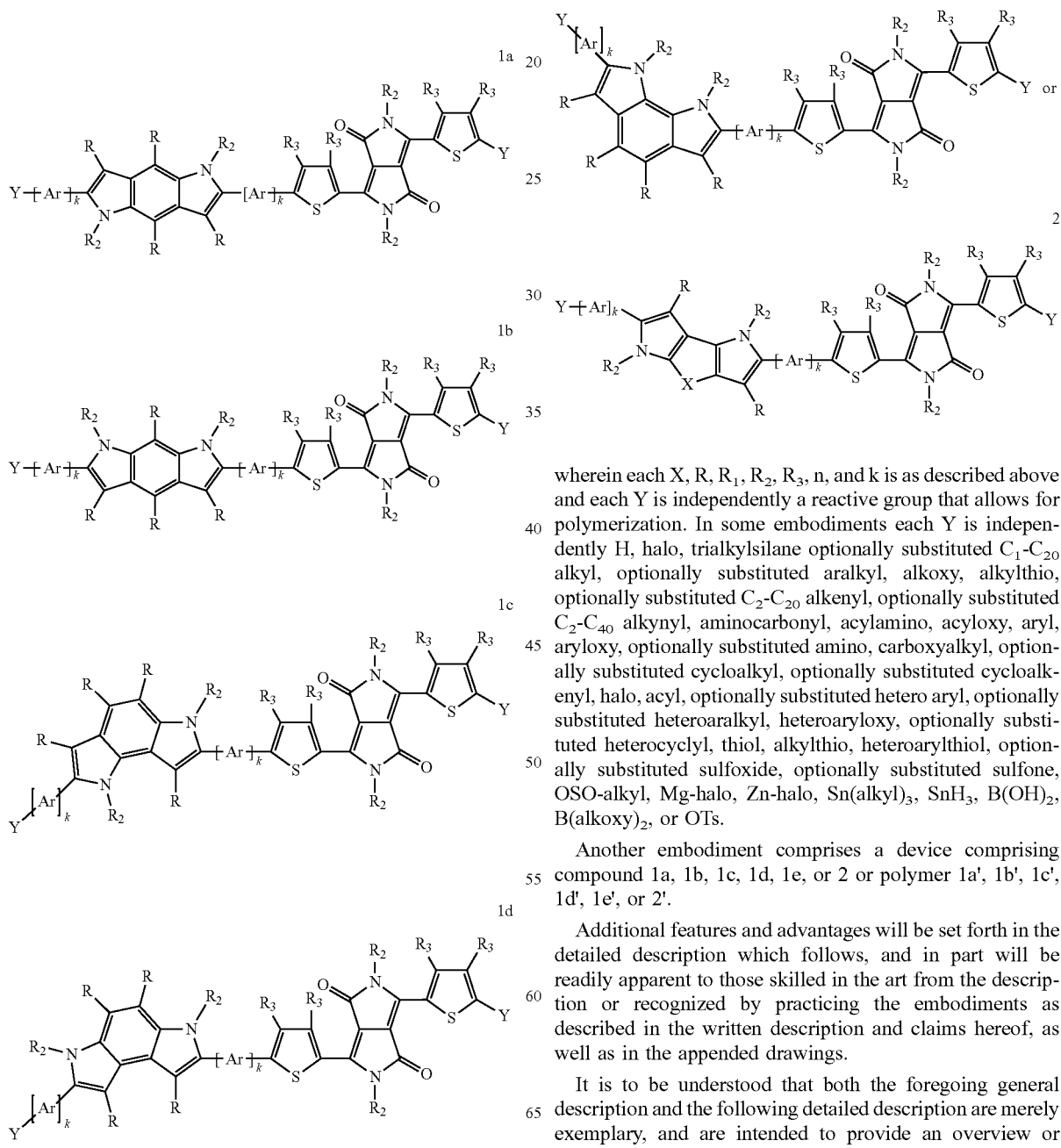

wherein each X, R, $R_1$, $R_2$, $R_3$, n, and k is as described above and each Y is independently a reactive group that allows for polymerization. In some embodiments each Y is independently H, halo, trialkylsilane optionally substituted $C_1$-$C_{20}$ alkyl, optionally substituted aralkyl, alkoxy, alkylthio, optionally substituted $C_2$-$C_{20}$ alkenyl, optionally substituted $C_2$-$C_{40}$ alkynyl, aminocarbonyl, acylamino, acyloxy, aryl, aryloxy, optionally substituted amino, carboxyalkyl, optionally substituted cycloalkyl, optionally substituted cycloalkenyl, halo, acyl, optionally substituted hetero aryl, optionally substituted heteroaralkyl, heteroaryloxy, optionally substituted heterocyclyl, thiol, alkylthio, heteroarylthiol, optionally substituted sulfoxide, optionally substituted sulfone, OSO-alkyl, Mg-halo, Zn-halo, Sn(alkyl)$_3$, SnH$_3$, B(OH)$_2$, B(alkoxy)$_2$, or OTs.

Another embodiment comprises a device comprising compound 1a, 1b, 1c, 1d, 1e, or 2 or polymer 1a', 1b', 1c', 1d', 1e', or 2'.

Additional features and advantages will be set forth in the detailed description which follows, and in part will be readily apparent to those skilled in the art from the description or recognized by practicing the embodiments as described in the written description and claims hereof, as well as in the appended drawings.

It is to be understood that both the foregoing general description and the following detailed description are merely exemplary, and are intended to provide an overview or framework for understanding.

BRIEF DESCRIPTION OF THE DRAWINGS

The accompanying drawings are included to provide a further understanding, and are incorporated in and constitute a part of this specification.

FIG. 1 is a graph of a simple mobility ranking metric based on linear combination of Neutral Dipole Moment and the inverse of the Reorganization Energy. Corresponding values for this metric have to be maximized for an optimal mobility property. Corning's previous polymer is at the Pareto Front 27 and is ranked lowest in this classification.

DETAILED DESCRIPTION

Before the present materials, articles, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19, 20, 30, or 40 carbon atoms, in some embodiments having 2 to 20 carbon atoms and more typically having 10 to 20 carbon atoms, wherein the number of carbons in the alkyl is designated by the range $C_a$-$C_b$, where "a" is the lower limit and "b" is the upper limit. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to: (1) an alkyl group as defined above, having 1, 2, 3, 4 or 5 substituents, typically 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO— alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2; or (2) an alkyl group as defined above that is interrupted by 1-10 atoms independently chosen from oxygen, sulfur and NR$_a$, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R$_{SO}$, in which R$_{SO}$ is alkyl, aryl, or heteroaryl and n is 0, 1 or 2; or (3) an alkyl group as defined above that has both 1, 2, 3, 4 or 5 substituents as defined above and is also interrupted by 1-10 atoms as defined above.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, typically 1-10 carbon atoms, more typically 1, 2, 3, 4, 5 or 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to: (1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO— alkyl, —SO-aryl, —SO-heteroaryl, —SO$_2$-alkyl, —SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2; or (2) an alkylene group as defined above that is interrupted by 1-20 atoms independently chosen from oxygen, sulfur and NR$_a$—, where R$_a$ is chosen from hydrogen, optionally substituted alkyl, cycloalkyl, cycloalkenyl, aryl, heteroaryl and heterocyclyl, or groups selected from carbonyl, carboxyester, carboxyamide and sulfonyl; or (3) an alkylene group as defined above that has both 1, 2, 3, 4 or 5 substituents as defined above and is also interrupted by 1-20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is an optionally substituted alkyl or optionally substituted cycloalkyl, or R is a group -Q-Z, in which Q is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Typical alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "alkylthio" refers to the group $R_S$—S—, where $R_S$ is as R is defined for alkoxy.

The term "alkenyl" refers to a monoradical of a branched or unbranched unsaturated hydrocarbon group typically having from 2 to 40 carbon atoms, more typically 2 to 20 carbon atoms and even more typically 2 to 10 carbon atoms and having 1-6, typically 1, double bond (vinyl). Typical alkenyl groups include ethenyl or vinyl (—CH=$CH_2$), 1-propylene or allyl (—$CH_2$CH=$CH_2$), isopropylene (—C($CH_3$)=$CH_2$), bicyclo[2.2.1]heptene, and the like. In the event that alkenyl is attached to nitrogen, the double bond cannot be alpha to the nitrogen.

The term "substituted alkenyl" refers to an alkenyl group as defined above having 1, 2, 3, 4 or 5 substituents, and typically 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO— alkyl, —SO-aryl, —SO— heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —S(O)$_n$$R_{SO}$, where $R_{SO}$ is alkyl, aryl, or heteroaryl and n is 0, 1 or 2.

The term "alkynyl" refers to a monoradical of an unsaturated hydrocarbon, typically having from 2 to 40 carbon atoms, more typically 2 to 20 carbon atoms and even more typically 2 to 10 carbon atoms and having at least 1 and typically from 1-6 sites of acetylene (triple bond) unsaturation. Typical alkynyl groups include ethynyl, (—C≡CH), propargyl (or prop-1-yn-3-yl, —$CH_2$C≡CH), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents, and typically 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —S(O)$_n$$R_{SO}$, where $R_{SO}$ is alkyl, aryl, or heteroaryl and n is 0, 1 or 2.

The term "aminocarbonyl" refers to the group —C(O)$NR_NR_N$ where each $R_N$ is independently hydrogen, alkyl, aryl, heteroaryl, heterocyclyl or where both $R_N$ groups are joined to form a heterocyclic group (e.g., morpholino). Unless otherwise constrained by the definition, all substituents may optionally be further substituted by 1-3 substituents chosen from alkyl, carboxy, carboxyalkyl, aminocarbonyl, hydroxy, alkoxy, halogen, —$CF_3$, amino, substituted amino, cyano, and —S(O)$_n$$R_{SO}$, where $R_{SO}$ is alkyl, aryl, or heteroaryl and n is 0, 1 or 2.

The term "acylamino" refers to the group —$NR_{NCO}$C(O)R where each $R_{NCO}$ is independently hydrogen, alkyl, aryl, heteroaryl, or heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$$R_{SO}$, where $R_{SO}$ is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxy, carboxyalkyl, aminocarbonyl, hydroxy, alkoxy, halogen, —$CF_3$, amino, substituted amino, cyano, and —S(O)$_n$$R_{SO}$, where $R_{SO}$ is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Typical aryls include phenyl, naphthyl and the like.

Unless otherwise constrained by the definition for the aryl substituent, such aryl groups can optionally be substituted with from 1 to 5 substituents, typically 1 to 3 substituents, selected from the group consisting of alkyl, alkenyl, alkynyl, alkoxy, cycloalkyl, cyclo alkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO— heteroaryl, —$SO_2$-alkyl, $SO_2$-aryl and —$SO_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$$R_{SO}$, where $R_{SO}$ is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group aryl-S—, where aryl is as defined as above.

The term "amino" refers to the group —$NH_2$.

The term "substituted amino" refers to the group —$NR_wR_w$ where each $R_w$ is independently selected from the group consisting of hydrogen, alkyl, cycloalkyl, carboxyalkyl (for example, benzyloxycarbonyl), aryl, heteroaryl and heterocyclyl provided that both $R_w$ groups are not hydrogen, or a group —Y—Z, in which Y is optionally substituted alkylene and Z is alkenyl, cycloalkenyl, or alkynyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "carboxyalkyl" refers to the groups —C(O)O-alkyl or —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, and —S(O)$_n$R$_{SO}$, in which R$_{SO}$ is alkyl, aryl, or heteroaryl and n is 0, 1 or 2.

The term "cycloalkyl" refers to carbocyclic groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, bicyclo[2.2.1] heptane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like.

The term "cycloalkenyl" refers to carbocyclic groups of from 3 to 20 carbon atoms having a single cyclic ring or multiple condensed rings with at least one double bond in the ring structure.

The terms "substituted cycloalkyl" or "substituted cycloalkenyl" refer to cycloalkyl or cycloalkenyl groups having 1, 2, 3, 4 or 5 substituents, and typically 1, 2, or 3 substituents, selected from the group consisting of alkyl, alkenyl, alkynyl, alkoxy, cycloalkyl, cyclo alkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "halogen" or "halo" refers to a fluoro, bromo, chloro, and iodo substituent.

The term "acyl" denotes a group —C(O)R$_{CO}$, in which R$_{CO}$ is hydrogen, optionally substituted alkyl, optionally substituted cycloalkyl, optionally substituted heterocyclyl, optionally substituted aryl, and optionally substituted heteroaryl.

The term "heteroaryl" refers to a radical derived from an aromatic cyclic group (i.e., fully unsaturated) having 1, 2, 3, 4, 5, 6, 7, 8, 9, 10, 11, 12, 13, 14, or 15 carbon atoms and 1, 2, 3 or 4 heteroatoms selected from oxygen, nitrogen and sulfur within at least one ring. Such heteroaryl groups can have a single ring (e.g., pyridyl or furyl) or multiple condensed rings (e.g., indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, thiophene, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, triazole, oxazole, thiazole, naphthyridine, and the like as well as N-oxide and N-alkoxy derivatives of nitrogen containing heteroaryl compounds, for example pyridine-N-oxide derivatives.

Unless otherwise constrained by the definition for the heteroaryl substituent, such heteroaryl groups can be optionally substituted with 1 to 5 substituents, typically 1 to 3 substituents selected from the group consisting of alkyl, alkenyl, alkynyl, alkoxy, cycloalkyl, cyclo alkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonyl amino, heteroaryloxy, heterocyclyl, heterocyclooxy, hydroxyamino, alkoxyamino, nitro, —SO— alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, typically 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholino, piperidinyl, piperazino, dihydropyridino, and the like.

Unless otherwise constrained by the definition for the heterocyclyl substituent, such heterocyclyl groups can be optionally substituted with 1, 2, 3, 4 or 5, and typically 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "thiol" refers to the group —SH.

The term "substituted alkylthio" refers to the group —S—substituted alkyl.

The term "heteroarylthiol" refers to the group —S—heteroaryl wherein the heteroaryl group is as defined above including optionally substituted heteroaryl groups as also defined above.

The term "sulfoxide" refers to a group —S(O)R$_{SO}$, in which R$_{SO}$ is alkyl, aryl, or heteroaryl. "Substituted sulfoxide" refers to a group —S(O)R$_{SO}$, in which R$_{SO}$ is substituted alkyl, substituted aryl, or substituted heteroaryl, as defined herein.

The term "sulfone" refers to a group —S(O)$_2$R$_{SO}$, in which R$_{SO}$ is alkyl, aryl, or heteroaryl. "Substituted sulfone" refers to a group —S(O)$_2$R$_{SO}$, in which R$_{SO}$ is substituted alkyl, substituted aryl, or substituted heteroaryl, as defined herein.

The term "keto" refers to a group —C(O)—.
The term "thiocarbonyl" refers to a group —C(S)—.
The term "carboxy" refers to a group —C(O)OH.

The term "conjugated group" is defined as a linear, branched or cyclic group, or combination thereof, in which p-orbitals of the atoms within the group are connected via delocalization of electrons and wherein the structure can be described as containing alternating single and double or triple bonds and may further contain lone pairs, radicals, or carbenium ions. Conjugated cyclic groups may comprise both aromatic and non-aromatic groups, and may comprise polycyclic or heterocyclic groups, such as diketopyrrolopyrrole. Ideally, conjugated groups are bound in such a way as to continue the conjugation between the thiophene moieties they connect.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Embodiments comprise rationally designed compounds and polymers comprising optionally-substituted dihydropyrroloindoles ("DHPI"), dipyrrolothiophenes or fused pyrroles (all generally referred to as "pyrrole groups" herein) bridged to optionally substituted diketopyrrolopyrroles ("DPP"). The materials have advantages over DPP alone in that they are soluble in non-chlorinated solvents, efficiently synthesized, and show very high mobilities in non-chlorinated solvents. Further, the compounds are relatively easy to modify and substituents can be introduced to multiple positions which allows for fine tuning material packing behaviors.

In one aspect, described herein are compositions comprising the formula 1a, 1b, 1c, 1d, 1e, or 2:

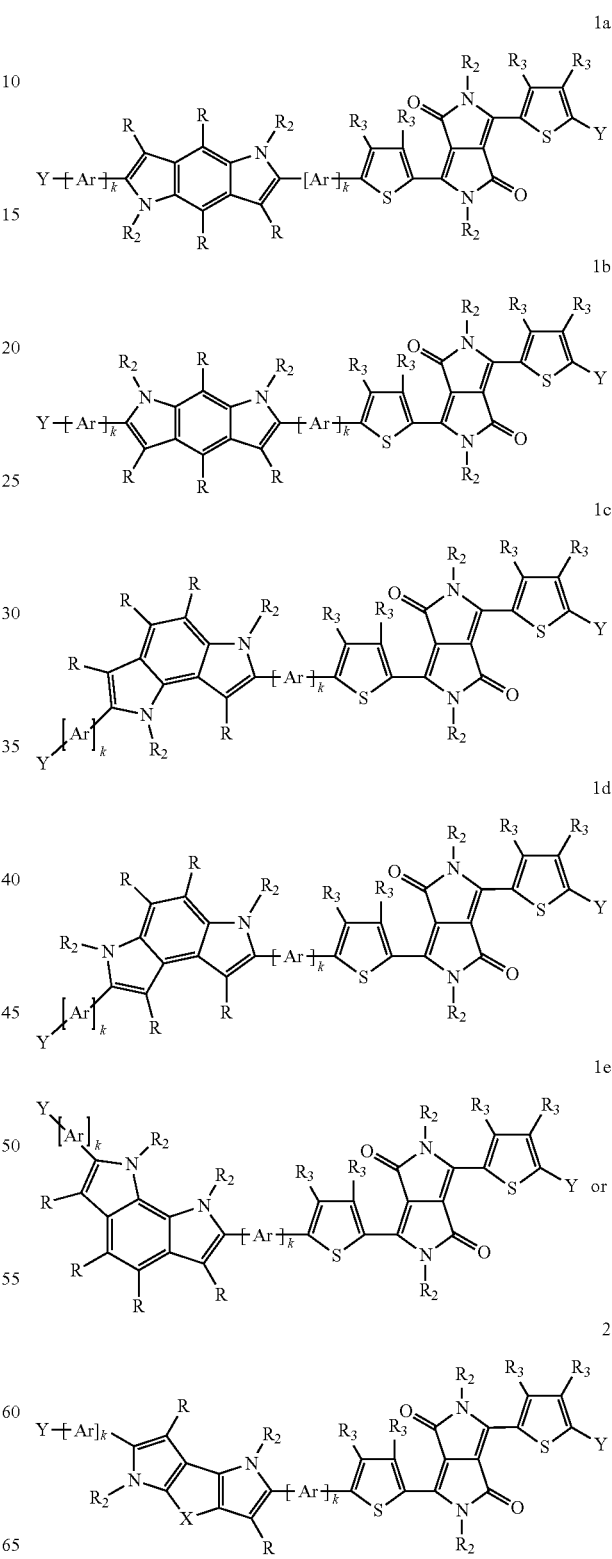

wherein Ar is an optionally substituted aromatic or heteroaromatic group or conjugated group; k is an integer from 0 to 5 with the proviso that when k is 0, the structure results in a direct bond between the thiophene and pyrrole group; each X is independently $NR_1$, $PR_1$, $AsR_1$, Sb, O, S, Te, or Se, with the proviso that due to conjugation, X may be bonded to one or more additional $R_1$; each Y is independently H, halo, trialkylsilane, optionally substituted $C_1$-$C_{40}$ alkyl, optionally substituted aralkyl, alkoxy, alkylthio, optionally substituted $C_2$-$C_{40}$ alkenyl, optionally substituted $C_2$-$C_{40}$ alkynyl, aminocarbonyl, acylamino, acyloxy, aryl, aryloxy, optionally substituted amino, carboxyalkyl, optionally substituted cycloalkyl, optionally substituted cycloalkenyl, halo, acyl, optionally substituted heteroaryl, optionally substituted heteroaralkyl, heteroaryloxy, optionally substituted heterocyclyl, thiol, alkylthio, heteroarylthio, optionally substituted sulfoxide, optionally substituted sulfone, OSO-alkyl, Mg-halo, Zn-halo, $Sn(alkyl)_3$, $SnH_3$, $B(OH)_2$, $B(alkoxy)_2$, or OTs; each R, $R_1$, $R_2$, and $R_3$ is independently H, halo, optionally substituted $C_1$-$C_{40}$ alkyl, optionally substituted aralkyl, alkoxy, alkylthio, optionally substituted $C_2$-$C_{40}$ alkenyl, optionally substituted $C_2$-$C_{40}$ alkynyl, aminocarbonyl, acylamino, acyloxy, optionally substituted aryl, aryloxy, optionally substituted amino, carboxyalkyl, optionally substituted cycloalkyl, optionally substituted cycloalkenyl, halo, acyl, optionally substituted hetero aryl, optionally substituted heteroaralkyl, heteroaryloxy, optionally substituted heterocyclyl, thiol, alkylthio, heteroarylthio, optionally substituted sulfoxide, or optionally substituted sulfone.

In some embodiments, the compound comprises 1a or 1b. In other embodiments, the compound comprises 1c or 1d, or 1e. In still other embodiments, the compound comprises 2. In some embodiments, X is $NR_1$, $PR_1$, $AsR_1$, Sb, O, S, Se, or Te with the proviso that due to conjugation, X may be bonded to one or more additional $R_1$; and each R, $R_1$, $R_2$, and $R_3$ is independently H, halo, optionally substituted $C_1$-$C_{40}$ alkyl, optionally substituted aralkyl, alkoxy, alkylthio, optionally substituted $C_2$-$C_{40}$ alkenyl, optionally substituted $C_2$-$C_{40}$ alkynyl, aminocarbonyl, acylamino, acyloxy, optionally substituted aryl, aryloxy, optionally substituted amino, carboxyalkyl, optionally substituted cycloalkyl, optionally substituted cycloalkenyl, halo, acyl, optionally substituted heteroaryl, optionally substituted heteroaralkyl, heteroaryloxy, optionally substituted heterocyclyl, thiol, alkylthio, heteroarylthio, optionally substituted sulfoxide, or optionally substituted sulfone.

In some embodiments, each R, $R_1$, $R_2$, and $R_3$ is independently H, optionally substituted alkyl, halo, optionally substituted alkenyl, optionally substituted alkynyl, optionally substituted aryl, optionally substituted heteroaryl, optionally substituted heteroaralkyl, optionally substituted cycloalkyl, optionally substituted cycloalkenyl, optionally substituted heterocyclyl, or aralkyl.

In some embodiments, each R, $R_1$, $R_2$, and $R_3$ is independently H, halo, optionally substituted alkyl, optionally substituted alkenyl, optionally substituted alkynyl, optionally substituted cycloalkyl, optionally substituted cycloalkenyl, optionally substituted heterocyclyl, or optionally substituted phenyl, optionally substituted thiophenyl, optionally substituted furanyl, optionally substituted pyrrolyl, optionally substituted imidazolyl, optionally substituted triazolyl, optionally substituted oxazolyl, optionally substituted thiazolyl, optionally substituted napthalenyl, optionally substituted isoquinolinyl, optionally substituted quinolinyl, or optionally substituted naphthyridinyl.

In some embodiments, each $R_2$ is independently H, optionally substituted alkyl, or halo. In particular, due to improvements in solubility and other factor, it is advantageous in some embodiments to have at least one or more of R, $R_2$, or $R_3$ independently be an optionally substituted $C_1$-$C_{20}$ alkyl or $C_2$-$C_{20}$ alkenyl, and in particular an optionally substituted branched $C_1$-$C_{20}$ alkyl or $C_2$-$C_{20}$ alkenyl. Particular embodiments may have optionally substituted $C_1$-$C_{20}$ alkyl groups only on one or more $R_2$ groups, or alternatively only on one or more R groups.

In some embodiments, particularly where compounds 1a-1e and 2 are to be used in polymerization steps, each Y is independently H, halo, —OSO-alkyl, —Mg-halo, —Zn-halo, —$Sn(alkyl)_3$, —$SnH_3$, —$B(OH)_2$, or —$B(alkoxy)_2$.

Another aspect comprises methods of making compounds 1a-1e and 2. The formation of the dipyrrolopyrole (DPP) moiety can be done via the reaction scheme shown in Tieke et al., Beilstein, *J. Org. Chem.* 830 (2010), 25 *Chem. Mater.* 782 (2013), and U.S. application Ser. No. 13/665,055, all of which are herein incorporated by reference in their entireties. Generally, the reaction to form the DPP moiety is shown via the following reaction scheme (Scheme 1):

Scheme 1

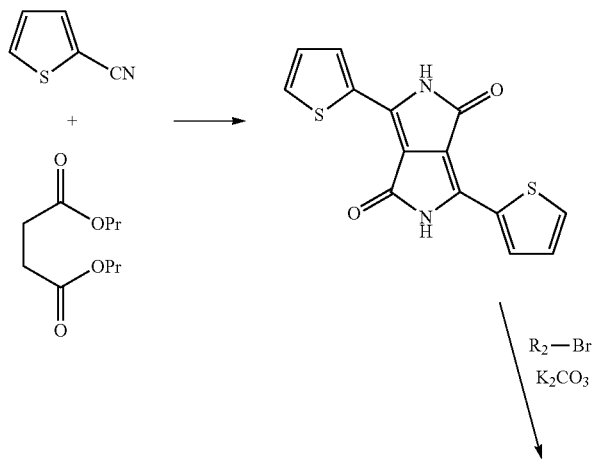

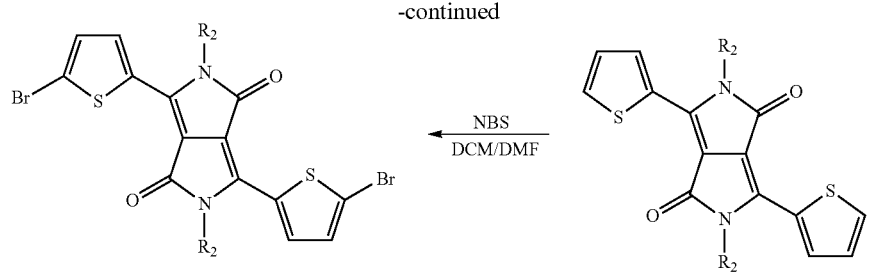

Formation of the pyrrole groups can be done via a number of chemical processes. For example, it can be done via cyclization of a diamine- or amide-modified benzene ring. A number of cyclization processes have been developed to prepare the DHPIs described herein. For example, in Scheme 2, a N,N'-1,4-Phenylenebis[2-chloro-N—$R_2$]acetamide is added to anhydrous aluminum chloride in an oil bath at ~200° C., cooled and filtered to produce the DHPI-dione shown.

Scheme 2

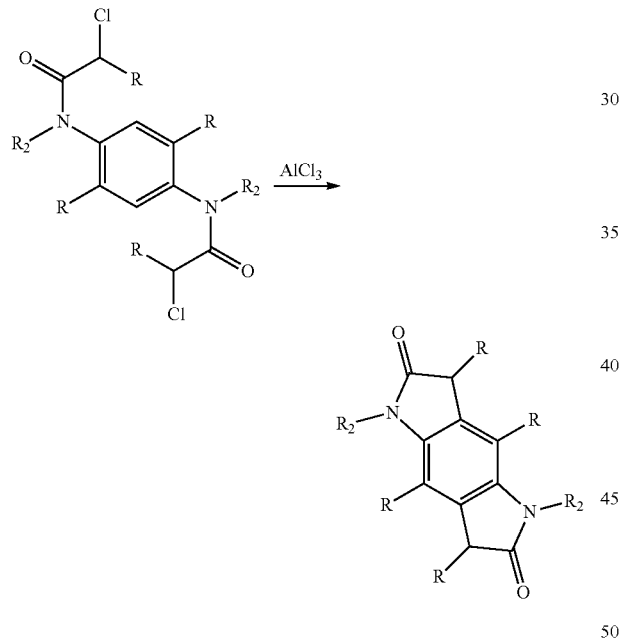

The DHPI-dione can be converted to a di-halo moiety via reaction (Scheme 3):

Scheme 3

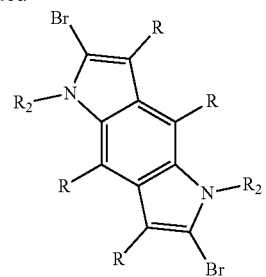

Similarly, $PCl_5$ can be used to make the chlorine-based equivalent of the structure in Scheme 3.

The modification nitrogen on the diindole group can be accomplished via the use of a base, such as potassium tert-butoxide (t-BuOK) in solvent (e.g., DMSO) followed by reaction with $R_2Br$ (Scheme 4):

Scheme 4

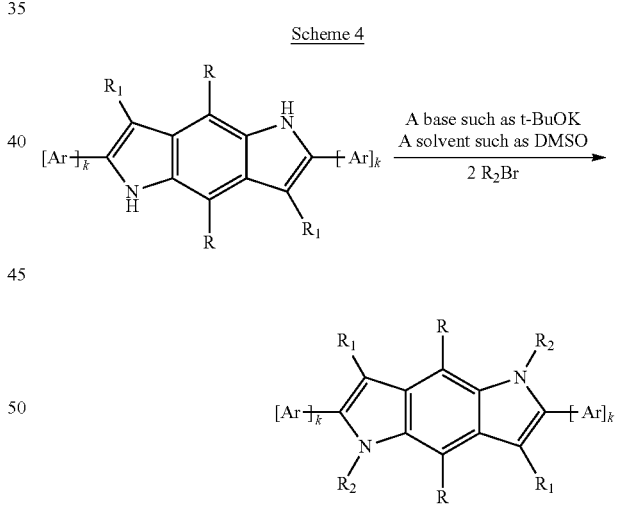

1a precursor

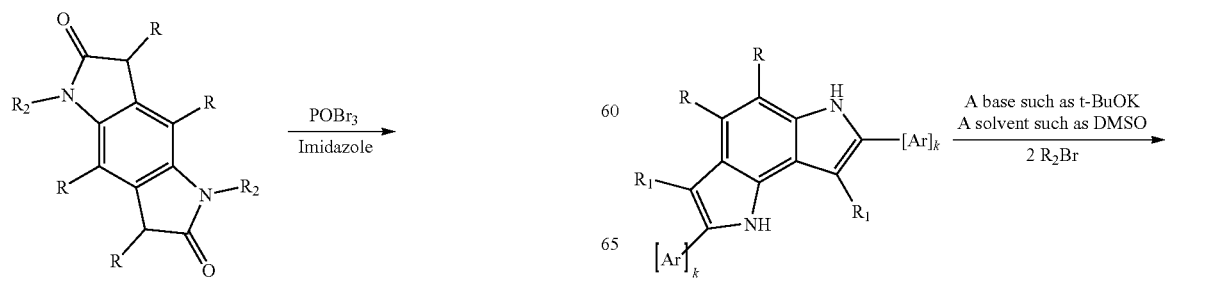

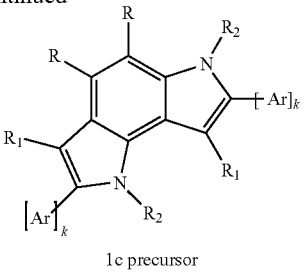

1c precursor

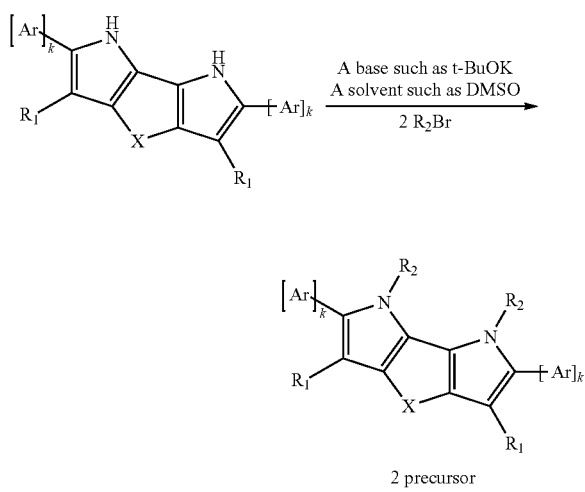

2 precursor where R, R₁, Ar, X, and k are as noted above. These reactions can also be applied to the other compounds disclosed herein.

Dibromination of the pyrrole groups can be accomplished using techniques developed by the inventors, see, e.g., PCT Int. Appl., 2011146308, herein incorporated by reference in its entirety, where a compounds such as N-bromosuccinimide is used to brominate the pyrrole groups through radical reaction (Scheme 5):

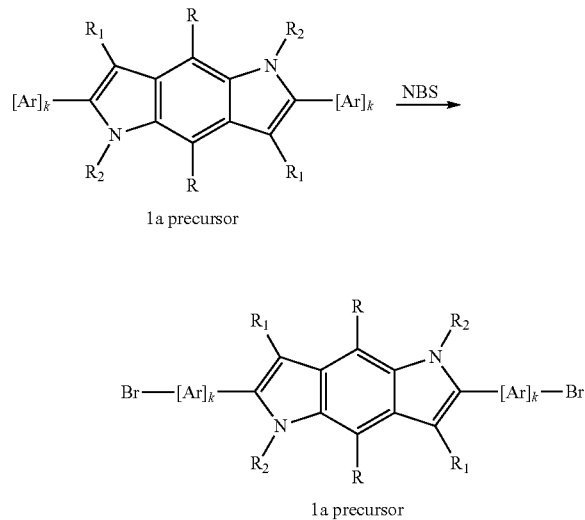

1a precursor

Likewise, precursors to compounds 1b-1e, and 2, may also be brominated in a similar fashion.

In some cases, it is advantageous to place a reactive tin group on the pyrrole groups. It is possible to obtain a ditin-modified pyrrole group via methods developed by the inventors, see, e.g., U.S. Pat. No. 8,278,346, herein incorporated by reference in its entirety. The ditin compound may be obtained either directly from reaction of a di-hydrogen compound or from the dibromo compound as shown in Scheme 6:

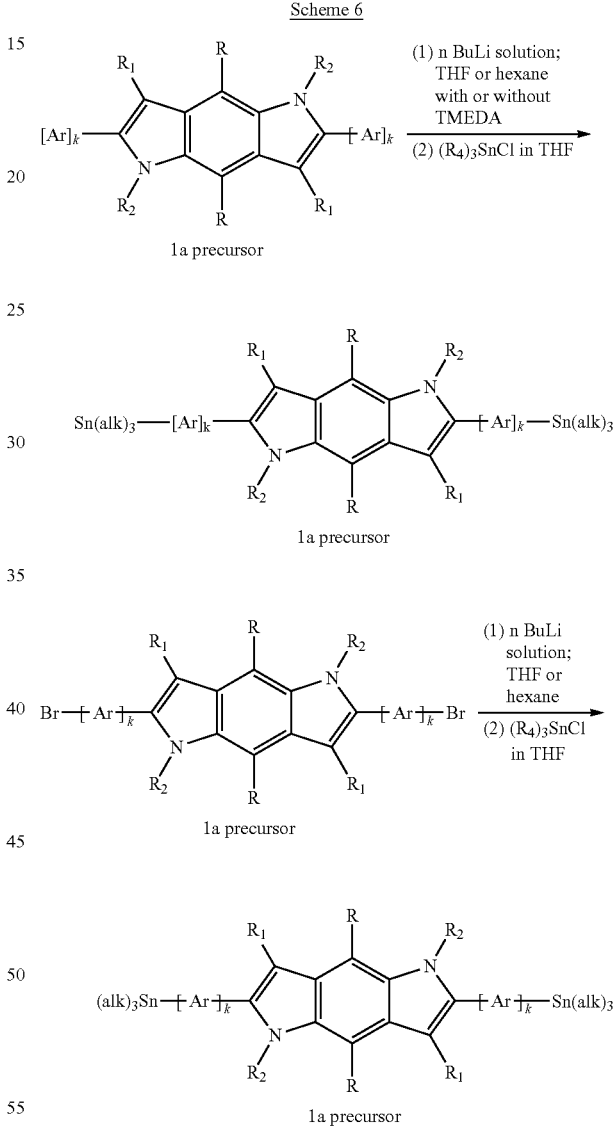

1a precursor

Likewise, the pyrrole groups in 1b-1e, and 2, may also be converted in a similar fashion.

In some embodiments, it may be advantageous to create a monomer of 1a-1e or 2. In such cases, it may be necessary to modify the chemistry of Scheme 6 to limit the formation of the ditin group to one side of the pyrrole compound. Modifications including the use of protecting groups or rendering reactive sites inactive is known in the art. Once the tin compound is formed, the pyrrole compound may be reacted with a bromo-modified DPP to produce compounds 1a-1e and 2. For example, a tin-modified compound of structure:

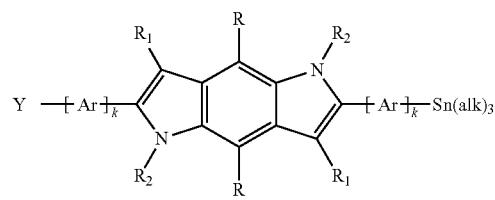

is reacted with a di-halo DPP of structure:

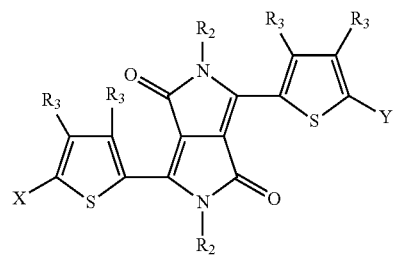

where X is halo and Ar, k, R, $R_1$, $R_2$, and $R_3$ are as defined above to produce structure 1a. This reaction is equally applicable to the other pyrrole structures in 1b-1e and 2.

In another aspect, the composition comprises a polymer comprising at least one moiety of formula 1a', 1b', 1c', 1d', 1e', or 2':

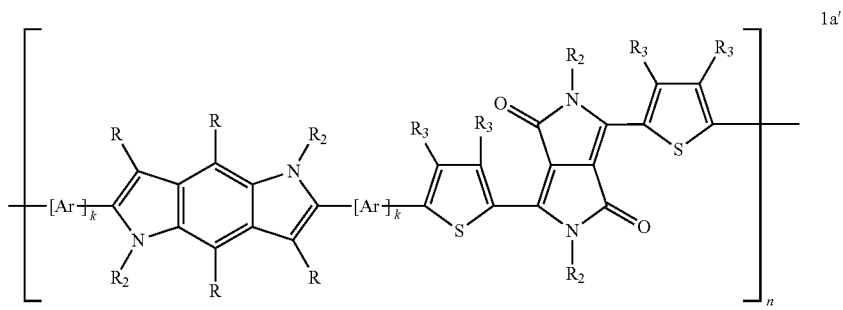

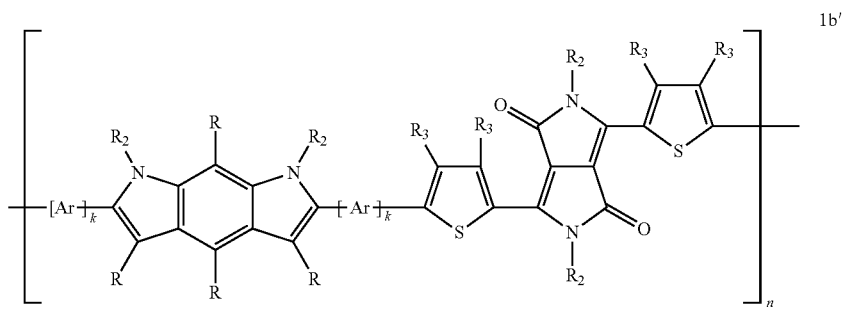

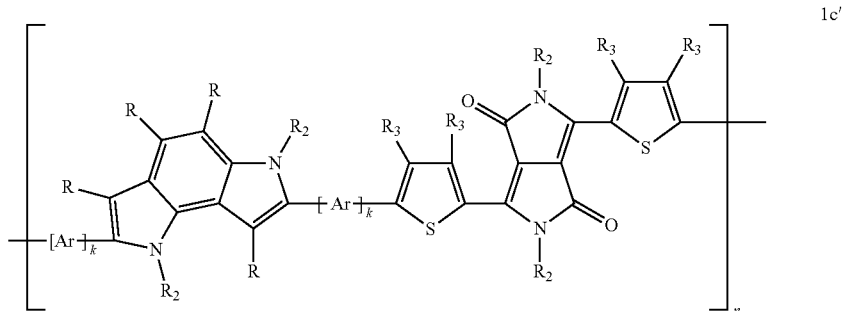

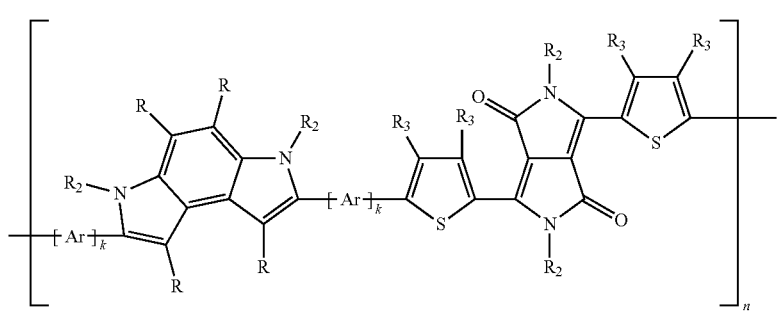

1d′

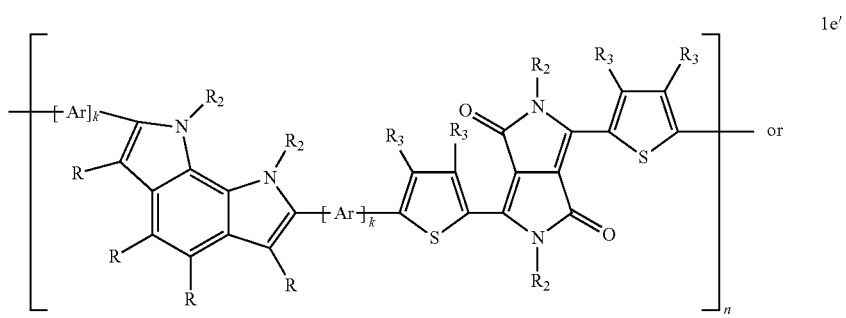

1e′ or

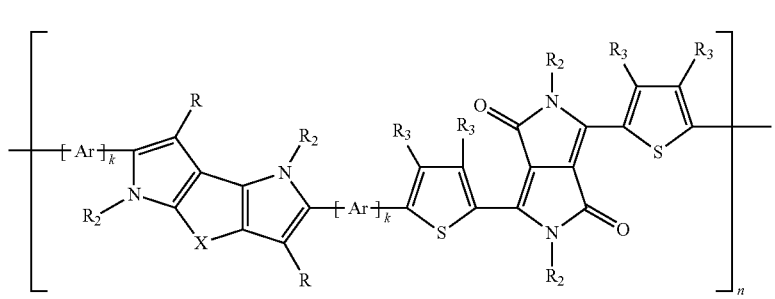

2′ wherein n is an integer greater than zero; X, Y, R, $R_1$, and $R_2$ all have the same meanings as above. In some embodiments, n is an integer from about 1 to 500. In some embodiments, n is an integer from about 3 to about 20, about 3 to about 15, about 3 to about 12, about 3 to about 10, or about 5 to about 9. In some embodiments, n is an integer about 1, 2, 3, 4, 5, 6, 7, 8, 9, 10, 11, 12, 13, 14, 15, 16, 17, 18, 19, 20, 30, 40, 50, 60, 70, 80, 90, 100, 150, 200, 250, 300, 350, 400, 450, or 500.

Another aspect comprises a method of making a polymer comprising at least one moiety of formula 1a′, 1b′, 1c′, 1d′, 1e′, or 2′:

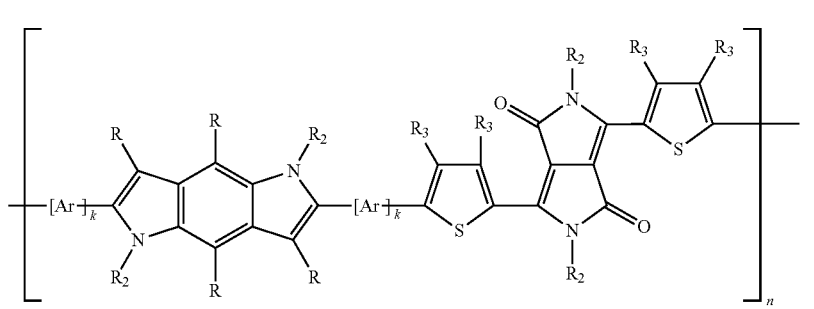

1a′

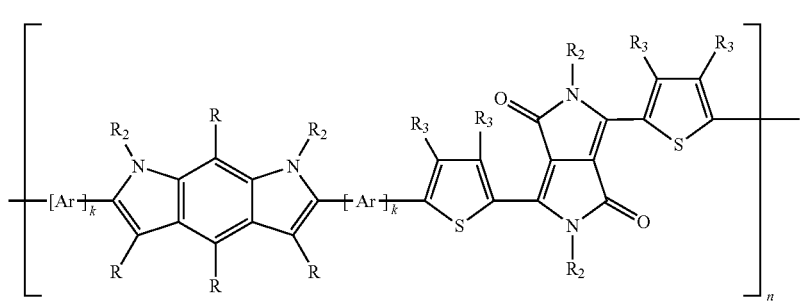
1b'
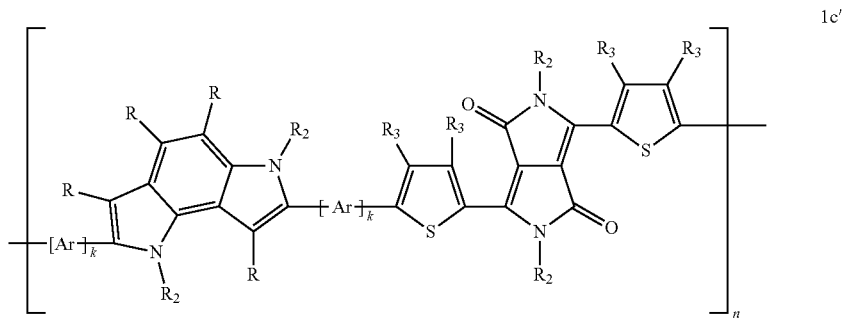
1c'
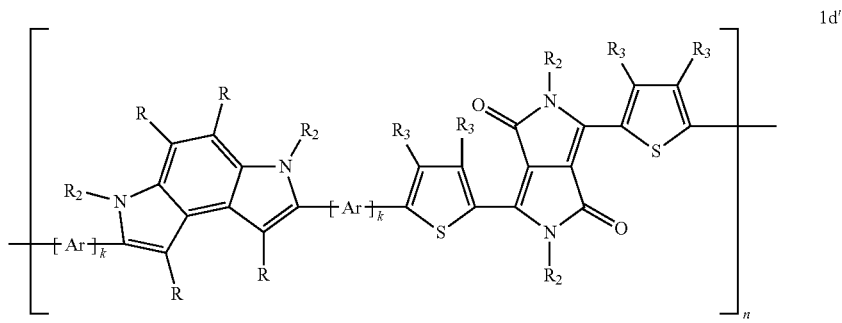
1d'
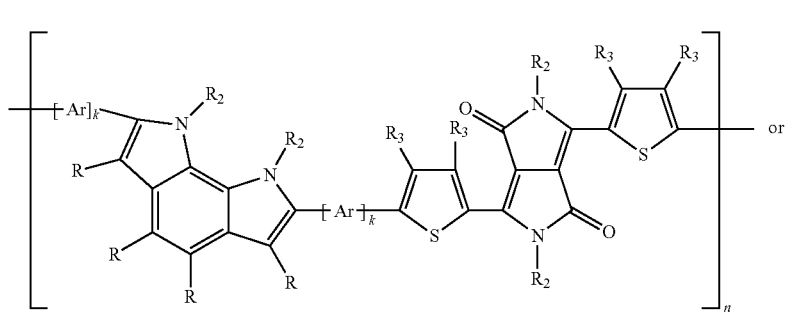
1e' or
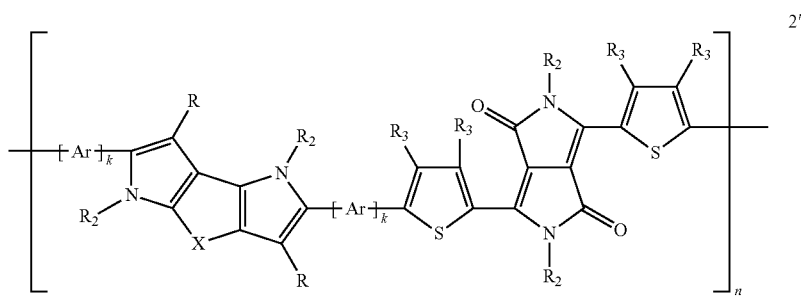
2' by respectively polymerizing a compound of structure:

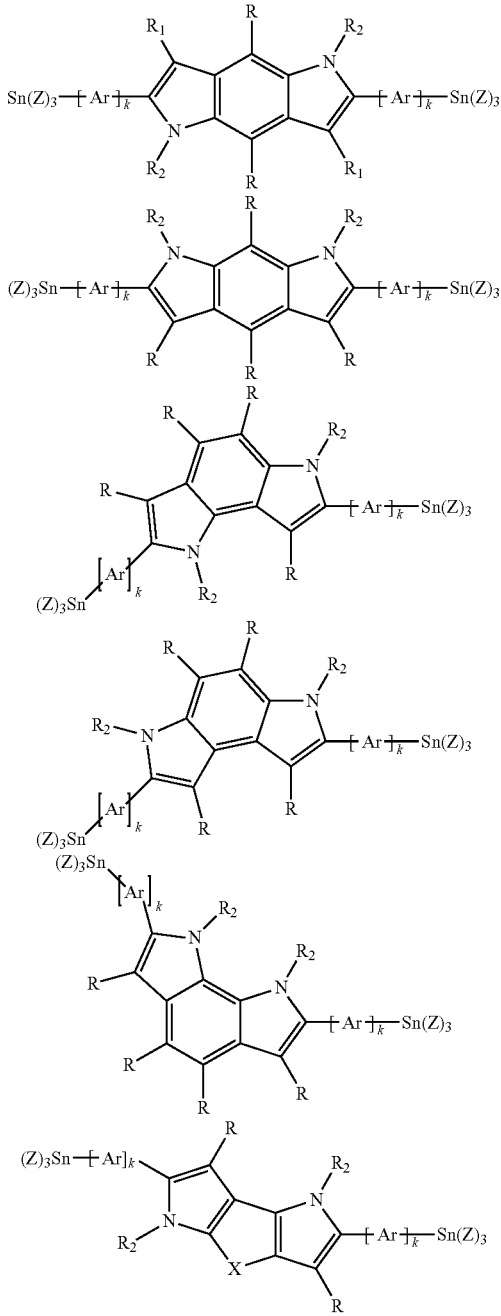

with a compound of structure:

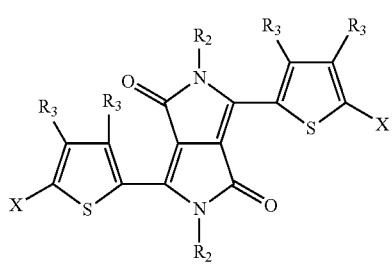

where X is halo and Z is H or an optionally substituted alkyl and n, X, Y, R, $R_1$, and $R_2$ all have the same meanings as above.

The polymerization may be done via a method similar to that shown in U.S. Pat. No. 8,278,346, herein incorporated by reference in its entirety. For example, a ditin compound of structure:

1a precursor

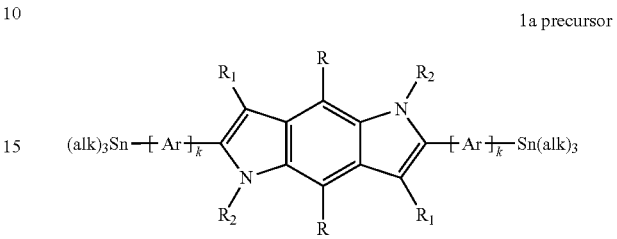

where is reacted with a di-halo DPP of structure:

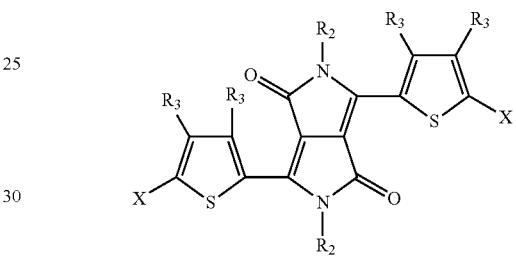

where X is halo and Ar, k, R, $R_1$, $R_2$, and $R_3$ are as defined above. This reaction is equally applicable to the other pyrrole structures of 1b-1e and 2.

Alternatively, in some embodiments, it may be possible to form the polymers directly from compounds 1a-1e and 2. For example, such embodiments may be made by forming two solutions of compounds 1a-1e and 2 with different reactive groups, for example where for one solution Y is a ditin moiety, and for a second solution Y is a dibromo moiety. Upon combination and reaction of the two solutions, polymerization leading to a polymer of 1a'-1e' or 2' would result.

In another aspect, embodiments herein are optimized for reorganization energy and mobility. In some embodiments, compounds embodied herein have improved solid state properties as a result of lower reorganization energy and/or higher mobility. In some embodiments, the properties of the compounds embodied herein may be described by Marcus theory (R. A. Marcus, 65 REV. MOD. PHYS. 599 (1993), herein incorporated by reference in its entirety).

Charge transport properties depend critically on the degree of ordering of the system or molecular ordering in the solid state, as well as the density of chemical impurities and/or structural defects such as grain size and dislocations. At the electronic level, two of the most important factors that control transport properties in organic conjugated materials are the interchain transfer integral β, and the reorganization energy λ. The transfer integral expresses the ease of transfer of a charge between interacting chains. The reorganization energy term describes the strength of the electron-phonon coupling. It is proportional to the geometric relaxation energy of the charged molecule over the individual neutral unit. In the context of semi-classical electron-transfer theory, the electron-transfer (hopping) rate can be expressed from Marcus theory in a simplified way as:

$$k_{et} = \frac{4\pi^2}{h} \frac{1}{\sqrt{4\pi k_B \lambda T}} \beta^2 e^{-\frac{\lambda}{4k_B T}} \quad (1)$$

(R. A. Marcus, 65 REV. MOD. PHYS. 599 (1993), herein incorporated by reference in its entirety) where T is the temperature, $\lambda$ is the reorganization energy, $\beta$ is the transfer integral, and h and $k_B$ are the Planck and Boltzmann constants, respectively.

It is possible to simplify equation (1) to:

$$k_{et}^{simple} = \frac{1}{\sqrt{\lambda}} \beta^2 e^{-\lambda} \quad (2)$$

in order to characterize the relative influence of both parameters $\lambda$ and $\beta$ to the charge transport rate. As can be seen from equation (2), the difference in mobility for different transfer integrals, $\beta$, is only significant for small values of the reorganization energy, $\lambda$. A big increase in the transfer integral does not yield a significant variation in the mobility, unless the reorganization energies are small. This implies that any optimization of the mobility should start with the design of single molecules with very low reorganization energy.

The reorganization energy includes two contributions that are associated with charge hopping. One is introduced by the geometric changes within the single molecule, and is denoted the internal part. The second one arises from the repolarization changes of the surrounding medium and is usually much smaller than the first one. In studies to qualitatively order molecules, it is generally valid to neglect this last contribution in the evaluation of the reorganization energy as no significant solvent reorganization occurs during the charge transfer in the condensed phase.

Table 1 incorporates reorganization energies for a number of embodiments. For each molecule, the geometry is optimized using quantum mechanics for both neutral and ionic states. Consequently, the basic hopping step in a molecular wire is defined by four energies: $E_0$ and $E_+$ represent the energies of the neutral and cation species in their lowest energy geometries, respectively, while $E_0^*$ and $E_+^*$ represent the energies of the neutral and cation species with the geometries of the cation and neutral species, respectively. The table provides neutral total dipole for the molecule, the vertical ionization potential, the hole reorganization energy, and the Pareto Front.

The quantum mechanics calculations to determine these above mentioned quantities used the experimentally parameterized Hamiltonian PM6 implemented in VAMP® semi-empirical molecular orbital software (Accelrys Software Inc.). Pentacene was used as the reference to validate the Hole Reorganization Energy calculations. Experimental data for Pentacene RE was ~0.12 eV (see M. Malagoli and J. L. Bredas, 327 CHEM. PHYS. LETT. 13 (2000) and N. W. Gruhn et al., 89 PHYS. REV. LETT. 275503 (2002), both hereby incorporated by reference in their entirety), compared to 0.114 eV from our calculations based on VAMP® (Accelrys Software Inc.).

Hole Reorganization energies for embodiments may comprise from about 0 eV to about 0.75 eV. In some embodiments, the hole reorganization energy is from about 0.04 to about 0.75 eV. In some embodiments, the hole reorganization energy is 0.75 eV or less. In some embodiments, the hole reorganization energy is about 0.04, 0.05, 0.06, 0.07, 0.08, 0.09, 0.10, 0.11, 0.12, 0.13, 0.14, 0.15, 0.17, 0.19, 0.20, 0.22, 0.25, 0.27, 0.30, 0.31, 0.32, 0.33, 0.34, 0.35, 0.37, 0.40, 0.45, 0.50, 0.60, 0.70, or 0.75.

TABLE 1

| Compound | Neutral Total Dipole [D] | Vertical IP [eV] | Hole Reorg Energy [eV] | Pareto Front |
|---|---|---|---|---|
| 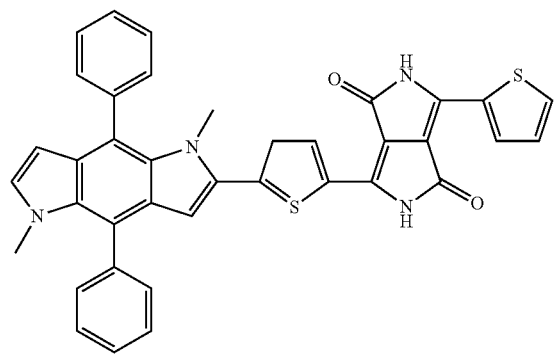 3-(5-(1,5-dimethyl-4,8-diphenyl-1,5-dihydropyrrolo[2,3-f]indol-2-yl)thiophen-2-yl)-6-(thiophen-2-yl)pyrrolo[3,4-c]pyrrole-1,4(2H,5H)-dione | 5.1790 | 6.6477 | 0.084295 | 1 |

TABLE 1-continued

| Compound | Neutral Total Dipole [D] | Vertical IP [eV] | Hole Reorg Energy [eV] | Pareto Front |
|---|---|---|---|---|
| 3-(5-(4,8-diphenyl-1,5-dihydropyrrolo[2,3-f]indol-2-yl)thiophen-2-yl)-6-(thiophen-2-yl)pyrrolo[3,4-c]pyrrole-1,4(2H,5H)-dione | 5.2820 | 6.9662 | 0.089012 | 2 |
| 3-(5-(1,5-dimethyl-1,5-dihydropyrrolo[2,3-f]indol-2-yl)thiophen-2-yl)-6-(thiophen-2-yl)pyrrolo[3,4-c]pyrrole-1,4(2H,5H)-dione | 3.1940 | 6.8983 | 0.099444 | 3 |
| 3-(5-(4,8-dimethyl-1,5-dihydropyrrolo[2,3-f]indol-2-yl)thiophen-2-yl)-6-(thiophen-2-yl)pyrrolo[3,4-c]pyrrole-1,4(2H,5H)-dione | 3.0520 | 6.8904 | 0.10484 | 4 |
| 3-(5-(1,4,5,8-tetraphenyl-1,5-dihydropyrrolo[2,3-f]indol-2-yl)thiophen-2-yl)-6-(thiophen-2-yl)pyrrolo[3,4-c]pyrrole-1,4(2H,5H)-dione | 6.8030 | 6.7374 | 0.10872 | 5 |

TABLE 1-continued

| Compound | Neutral Total Dipole [D] | Vertical IP [eV] | Hole Reorg Energy [eV] | Pareto Front |
|---|---|---|---|---|
| 3-(5-(1,5-dihydropyrrolo[2,3-f]indol-2-yl)thiophen-2-yl)-6-(thiophen-2-yl)pyrrolo[3,4-c]pyrrole-1,4(2H,5H)-dione | 3.0230 | 7.2784 | 0.11478 | 6 |
| Pentacene (comparative) | 0.012000 | 7.7531 | 0.11516 | 7 |
| 3-(5-(1,4,5,8-tetrahexyl-1,5-dihydropyrrolo[2,3-f]indol-2-yl)thiophen-2-yl)-6-(thiophen-2-yl)pyrrolo[3,4-c]pyrrole-1,4(2H,5H)-dione | 6.2260 | 6.5287 | 0.12915 | 8 |

TABLE 1-continued

| Compound | Neutral Total Dipole [D] | Vertical IP [eV] | Hole Reorg Energy [eV] | Pareto Front |
|---|---|---|---|---|
| 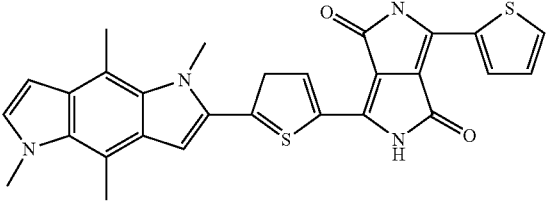<br>3-(5-(1,4,5,8-tetramethyl-1,5-dihydropyrrolo[2,3-f]indol-2-yl)thiophen-2-yl)-6-(thiophen-2-yl)pyrrolo[3,4-c]pyrrole-1,4(2H,5H)-dione | 3.2690 | 6.5633 | 0.12955 | 9 |
| 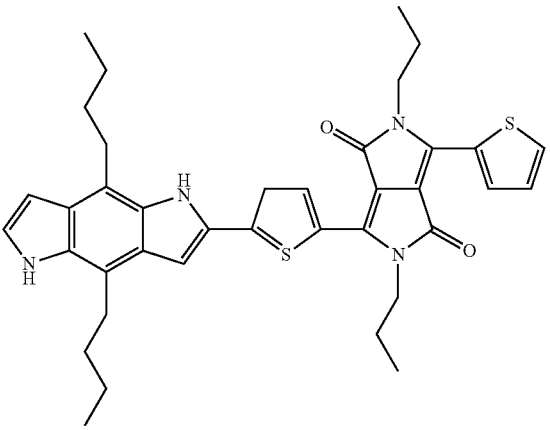<br>3-(5-(4,8-dibutyl-1,5-dihydropyrrolo[2,3-f]indol-2-yl)thiophen-2-yl)-2,5-dipropyl-6-(thiophen-2-yl)pyrrolo[3,4-c]pyrrole-1,4(2H,5H)-dione | 4.4890 | 6.7172 | 0.13477 | 10 |
| 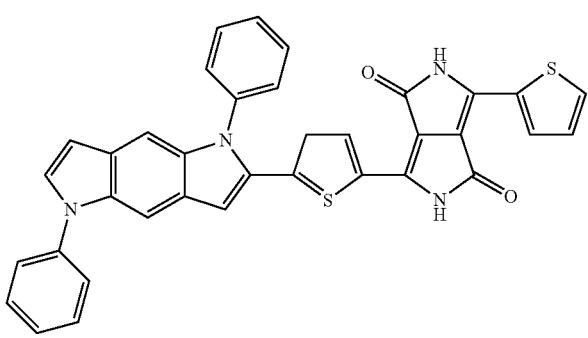<br>3-(5-(1,5-diphenyl-1,5-dihydropyrrolo[2,3-f]indol-2-yl)thiophen-2-yl)-6-(thiophen-2-yl)pyrrolo[3,4-c]pyrrole-1,4(2H,5H)-dione | 5.5240 | 6.9820 | 0.13575 | 11 |

TABLE 1-continued

| Compound | Neutral Total Dipole [D] | Vertical IP [eV] | Hole Reorg Energy [eV] | Pareto Front |
|---|---|---|---|---|
| 3-(5-(1,5-di(thiophen-2-yl)-1,5-dihydropyrrolo[2,3-f]indol-2-yl)thiophen-2-yl)-2,5-dipropyl-6-(thiophen-2-yl)pyrrolo[3,4-c]pyrrole-1,4(2H,5H)-dione | 1.6100 | 7.0450 | 0.14477 | 12 |
| 3-(5-(4,8-dihexyl-1,5-dimethyl-1,5-dihydropyrrolo[2,3-f]indol-2-yl)thiophen-2-yl)-6-(thiophen-2-yl)pyrrolo[3,4-c]pyrrole-1,4(2H,5H)-dione | 5.0320 | 6.5885 | 0.15718 | 13 |
| 3-(5-(4,7-dihydro-1,7-dimethyl-4-phenyl-1H-dipyrrolo[3,2-b:2′,3′-d]pyrrole-2-yl)thiophen-2-yl)-6-(thiophen-2-yl)pyrrolo[3,4-c]pyrrole-1,4(2H,5H)-dione | 7.9940 | 6.6464 | 0.16841 | 14 |

TABLE 1-continued
| Compound | Neutral Total Dipole [D] | Vertical IP [eV] | Hole Reorg Energy [eV] | Pareto Front |
|---|---|---|---|---|
| 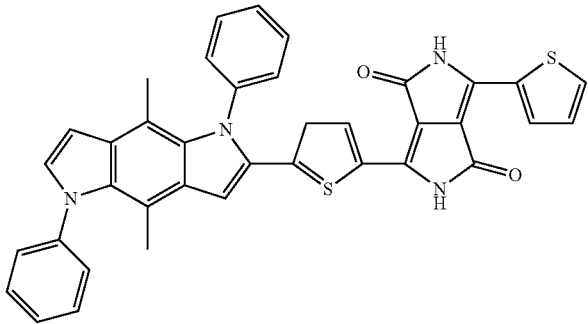<br>3-(5-(4,8-dimethyl-1,5-diphenyl-1,5-dihydropyrrolo[2,3-f]indol-2-yl)thiophen-2-yl)-6-(thiophen-2-yl)pyrrolo[3,4-c]pyrrole-1,4(2H,5H)-dione | 5.3830 | 6.6361 | 0.17426 | 15 |
| 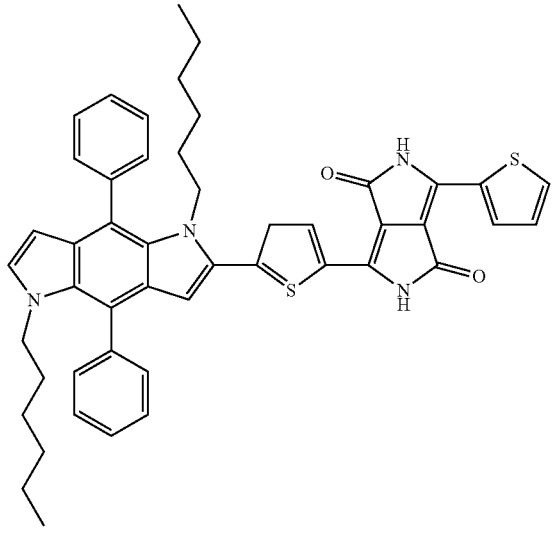<br>3-(5-(1,5-dihexyl-4,8-diphenyl-1,5-dihydropyrrolo[2,3-f]indol-2-yl)thiophen-2-yl)-6-(thiophen-2-yl)pyrrolo[3,4-c]pyrrole-1,4(2H,5H)-dione | 6.4620 | 6.7225 | 0.19448 | 16 |

TABLE 1-continued

| Compound | Neutral Total Dipole [D] | Vertical IP [eV] | Hole Reorg Energy [eV] | Pareto Front |
|---|---|---|---|---|
| 3-(5-(4,8-dihexyl-1,5-diphenyl-1,5-dihydropyrrolo[2,3-f]indol-2-yl)thiophen-2-yl)-6-(thiophen-2-yl)pyrrolo[3,4-c]pyrrole-1,4(2H,5H)-dione | 6.6250 | 6.5706 | 0.20366 | 17 |
| 3-(5-(1,5-dihexyl-4,8-dimethyl-1,5-dihydropyrrolo[2,3-f]indol-2-yl)thiophen-2-yl)-6-(thiophen-2-yl)pyrrolo[3,4-c]pyrrole-1,4(2H,5H)-dione | 5.5870 | 6.6298 | 0.24781 | 18 |
| 3-(5-(4,7-dihydro-4-methyl-1H-dipyrrolo[3,2-b:2′,3′-d]pyrrole-2-yl)thiophen-2-yl)-6-(thiophen-2-yl)pyrrolo[3,4-c]pyrrole-1,4(2H,5H)-dione | 3.6340 | 6.9565 | 0.32312 | 19 |

TABLE 1-continued

| Compound | Neutral Total Dipole [D] | Vertical IP [eV] | Hole Reorg Energy [eV] | Pareto Front |
|---|---|---|---|---|
| 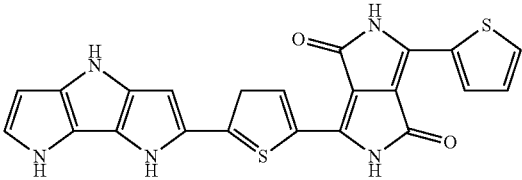<br>3-(5-(4,7-dihydro-1H-dipyrrolo[3,2-b:2',3'-d]pyrrole-2-yl)thiophen-2-yl)-6-(thiophen-2-yl)pyrrolo[3,4-c]pyrrole-1,4(2H,5H)-dione | 3.9920 | 7.0522 | 0.33319 | 20 |
| 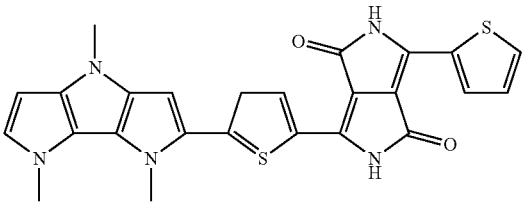<br>3-(5-(4,7-dihydro-1,4,7-trimethyl-1H-dipyrrolo[3,2-b:2',3'-d]pyrrole-2-yl)thiophen-2-yl)-6-(thiophen-2-yl)pyrrolo[3,4-c]pyrrole-1,4(2H,5H)-dione | 4.7780 | 6.7736 | 0.33917 | 21 |
| 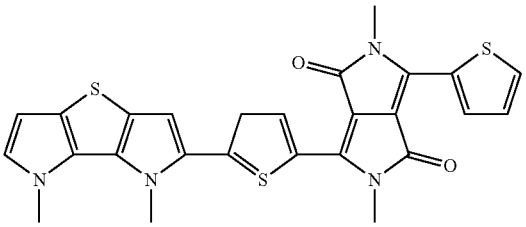<br>3-(5-(1,7-dihydro-1,7-dimethyl-thieno[3,2-b:4,5-b']dipyrrole-2-yl)thiophen-2-yl)-6-(thiophen-2-yl)pyrrolo[3,4-c]pyrrole-1,4(2H,5H)-dione | 5.5350 | 7.1914 | 0.33931 | 22 |
| 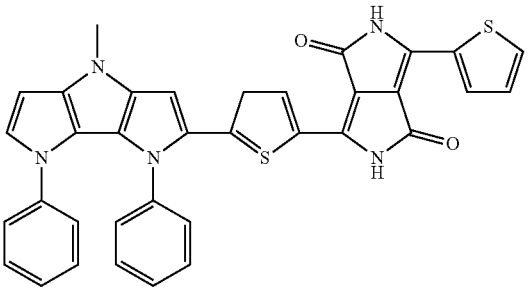<br>3-(5-(4,7-dihydro-1,7-diphenyl-4-methyl-1H-dipyrrolo[3,2-b:2',3'-d]pyrrole-2-yl)thiophen-2-yl)-6-(thiophen-2-yl)pyrrolo[3,4-c]pyrrole-1,4(2H,5H)-dione | 5.0060 | 6.7713 | 0.35348 | 23 |

TABLE 1-continued

| Compound | Neutral Total Dipole [D] | Vertical IP [eV] | Hole Reorg Energy [eV] | Pareto Front |
|---|---|---|---|---|
| 3-(5-(4,7-dihydro-1,7-diphenyl-1H-dipyrrolo[3,2-b:2',3'-d]pyrrole-2-yl)thiophen-2-yl)-6-(thiophen-2-yl)pyrrolo[3,4-c]pyrrole-1,4(2H,5H)-dione | 5.1560 | 6.8570 | 0.36994 | 24 |
| 3-(5-(4,7-dihydro-1,4,7-triphenyl-1H-dipyrrolo[3,2-b:2',3'-d]pyrrole-2-yl)thiophen-2-yl)-6-(thiophen-2-yl)pyrrolo[3,4-c]pyrrole-1,4(2H,5H)-dione | 6.7190 | 6.8271 | 0.37773 | 25 |
| 3-(5-(1,7-dihydro-1,7-dimethyl-furo[3,2-b:4,5-b']dipyrrole-2-yl)-2,5-dimethyl-6-(thiophen-2-yl)pyrrolo[3,4-c]pyrrole-1,4(2H,5H)-dione | 7.8630 | 7.1224 | 0.63376 | 26 |

TABLE 1-continued

| Compound | Neutral Total Dipole [D] | Vertical IP [eV] | Hole Reorg Energy [eV] | Pareto Front |
|---|---|---|---|---|
| 3-(5-(3,7-dihexyl-thieno[3,2-b]thieno[2′,3′:4,5]thieno[2,3-d]thiophene-2-yl)thiophen-2-yl)-6-(thiophen-2-yl)pyrrolo[3,4-c]pyrrole-1,4(2H,5H)-dione | 4.6680 | 7.7050 | 0.67130 | 27 |

The compositions described herein (monomers, oligomers, polymers) can be used to make a wide variety of devices. For example, the device can be a fused thiophene moiety-containing composition configured in an electronic, optoelectronic, or nonlinear optical device. The compositions described herein can also be used in field effect transistors (FETs), thin-film transistors (TFTs), organic light-emitting diodes (OLEDs), PLED applications, electro-optic (EO) applications, as conductive materials, as two photon mixing materials, as organic semiconductors, as non-linear optical (NLO) materials, as RFID tags, as electroluminescent devices in flat panel displays, in photovoltaic devices, and as chemical or biological sensors.

The polymers comprising the fused thiophene moieties described herein (1a', 1b', 1c', 1d', 1e', and 2') possess several advantages over similar compounds. The polymers embodied herein are easier to modify on the designed fused rings, allowing for improvements in the polymerization process and processability. Further, substituents can be introduced to multiple positions which can enable fine tuning material packing behaviors.

EXAMPLES

The methods disclosed herein are intended for purposes of exemplifying only and are not to be construed as limitations thereon. Those skilled in the art will appreciate that other synthetic routes may be used to synthesize the inventive compounds. Some aspects of some embodiments may be synthesized by synthetic routes that include processes analogous to those well-known in the chemical arts, particularly in light of the description contained herein. Although specific starting materials and reagents are depicted in the schemes and discussed below, other starting materials and reagents can be easily substituted to provide a variety of derivatives and/or reaction conditions. The starting materials are generally available from commercial sources, such as Aldrich Chemicals (Milwaukee, Wis.), or are readily prepared using methods well known to those skilled in the art (e.g., prepared by methods generally described in Louis F. Fieser and Mary Fieser, REAGENTS FOR ORGANIC SYNTHESIS, v. 1-19, Wiley, New York (1967-1999 ed.), or BEILSTEINS HANDBUCH DER ORGANISCHEN CHEMIE, 4, Aufl. ed. Springer-Verlag, Berlin, including supplements (also available via the Beilstein online database)). In addition, many of the compounds prepared by the methods described below can be further modified in light of this disclosure using conventional chemistry well known to those skilled in the art.

The following examples are put forth so as to provide those of ordinary skill in the art with a complete disclosure and description of how the materials, articles, and methods described and claimed herein are made and evaluated, and are intended to be purely exemplary and are not intended to limit the scope. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Although specific starting materials and reagents are depicted in the Examples below, other starting materials and reagents can be easily substituted to provide a variety of derivatives and/or reaction conditions. In addition, many of the compounds prepared by the methods described below can be further modified in light of this disclosure using conventional chemistry well known to those skilled in the art. Only reasonable and routine experimentation will be required to optimize such process conditions.

Example 1: N,N'-Didecahexylbenzene-1,4-diamine (1)

Cyclohexa 1,4-dione (6 g, 53.5 mmol) dissolved in ethanol at 50° C. is added to a solution of hexdecylamine 28.4 g (technical grade) in ethanol (500 ml) in a beaker. The solution is vigorously stirred for 2 h and the resulting suspension is filtered and washed twice with 50 mL of hot ethanol. The yield of the tan powder is 15.7 g (53%). $^1$H NMR (400 MHz, Chloroform-d) δ 6.54 (s, 4H), 3.02 (t, J=7.1 Hz, 4H), 1.57 (p, J=7.1 Hz, 4H), 1.39-1.24 (m, 52H), 0.92-0.82 (m, 6H); $^{13}$C NMR (101 MHz, CDCl$_3$) δ 140.91, 114.72, 45.0, 31.91, 29.77, 29.67, 29.60, 22.68, 14.11.

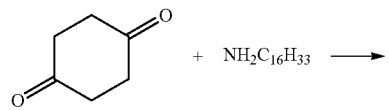

(1)

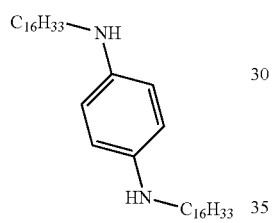

Example 2: N,N'-1,4-Phenylenebis[2-chloro-N-hexyl]acetamide (2)

A solution of 1 (10 g, 17.95 mmol) and 4-(dimethylamino)pyridine (DMAP) (4.39 g, 35.11 mmol) in THF (500 mL) is added drop wise to a solution of chloroacetyl chloride (6.08 g, 53.86 mmol) in THF (100 mL) at 0° C. After 1 h, the reaction mixture is concentrated to about 50 mL and quenched with water. The precipitate is collected by filtration. After being washed with water and methanol, the solid is dried in vacuo to yield 8.4 g (65%). $^1$H NMR (400 MHz, CDCl$_3$) δ 7.30 (s, 4H), 3.80 (s, 4H), 3.74-3.63 (m, 4H), 1.71 (m, 4H), 1.51 (d, J=7.6 Hz, 4H), 1.22 (m, J=4.3 Hz, 16H), 0.85 (t, J=6.7 Hz, 48H); $^{13}$C NMR (101 MHz, CDCl$_3$) δ 165.4, 140.35, 126.32, 51.56, 41.72, 31.89, 29.66, 29.63, 29.61, 29.55, 29.33, 29.27, 26.66, 22.89, 22.66, 14.10.

(2)

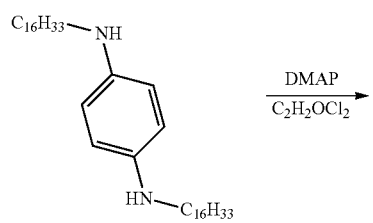

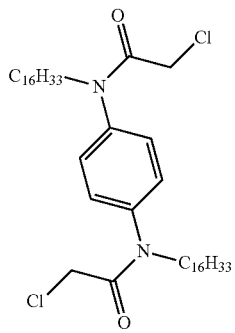

Example 3: 1,5-dihexadecyl-5,7-dihydropyrrolo[2,3-f]indole-2,6(1H,3H)-dione (3)

940 mg of anhydrous aluminum chloride is added to 1 g of 2. The mixture is paced in an oil bath at 190° C. for 1 h. After cooling, cracked ice is added to quench the reaction. The precipitate formed is collected by filtration. After being washed with water and methanol, the solid is dried and further purified by column chromatography on silica gel with DCM:ethyl acetate=10:1 as eluent to yield 3 (56 mg, 6%) as a brown solid. $^1$H NMR (400 MHz, CDCl$_3$) δ 6.75 (s, 4H), 3.60 (s, 4H), 1.82 (d, J=7.6 Hz, 4H), 1.22 (m, 16H), 0.86 (t, J=6.7 Hz, 48H); $^{13}$C NMR (101 MHz, CDCl$_3$) δ 175.4, 140.00, 123.32, 105.6 35.90, 31.89, 29.66, 29.63, 29.61, 29.55, 29.33, 29.81, 26.67, 22.89, 22.56, 14.10.

(3)

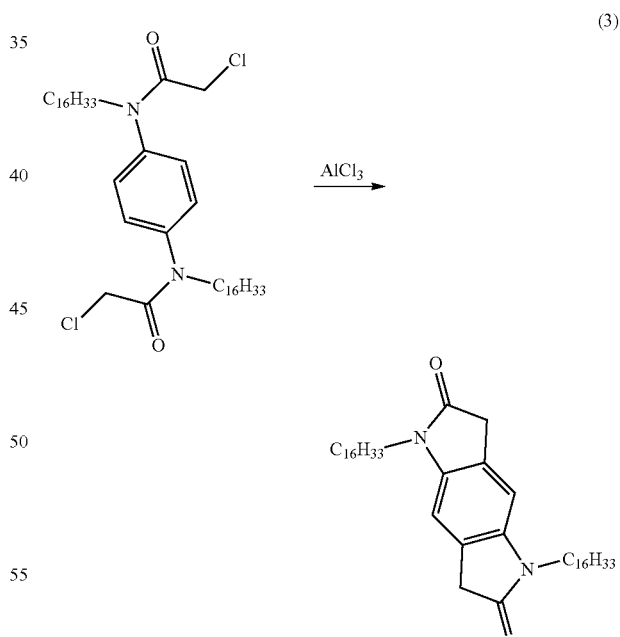

Example 4

A solution of 1 (0.2 g), t-NaOBu (0.22 g), Pd$_2$dba$_3$ (44 mg) and s-BINAP (120 mg) in dry toluene (6 mL) is purged with nitrogen for 20 min NH$_2$C$_5$H$_{11}$ (0.9 mL) is added via a syringe and the mixture is stirred under nitrogen at 110° C. for 30 min. After cooling to room temperature, water is added to the solution and the reaction mixture is extracted twice with diethyl ether. After the organic phases are dried over MgSO$_4$, the solvents are removed using a rotary evaporator. The crude product is purified by column chromatography and the desired product (4) is obtained as white solid (MS found=MS calculated=406).

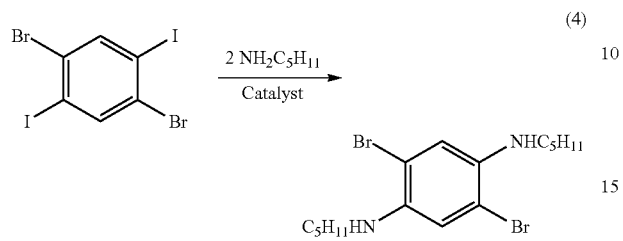

Example 5

(4) (116 mg) is mixed with CuI (3 mg), Pd(PPh$_3$)$_2$Cl$_2$ and TEA (6 mL) in an oven dried flask under Ar. The solution is degassed for 2-5 min. TMS-acetylene (0.4 mL) is added and the reaction mixture is stirred at 90° C. for 3.5 h. After cooling down to room temperature, the reaction mixture is filtered through celite, the solid residue is washed with EtOAc, and the combined organic phases are concentrated under reduced pressure. Flash column chromatography yields the desired target structure (5) (MS found=MS calculated=440).

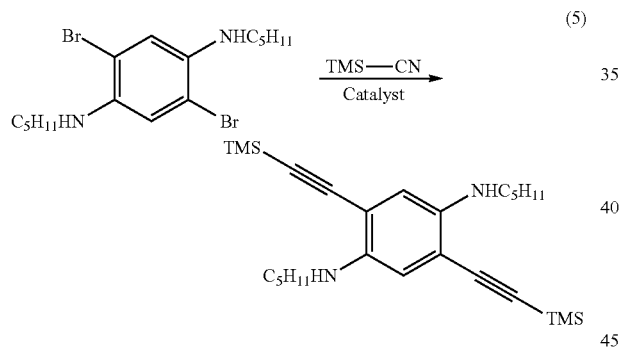

Example 6

TBAF is added to a solution of (5) (about 100 mg) in THF (2 mL) at 0° C. and the resulting solution is stirred for 30 min. H$_2$O is added to dilute the solution, and then the organic layer is separated, washed with brine, and dried over Na$_2$SO$_4$. The solvent is removed under reduced pressure and the residue is purified by silica gel column chromatography to afford (6) as major compounds along with (7) as a minor compound (MS found=MS calculated=296).

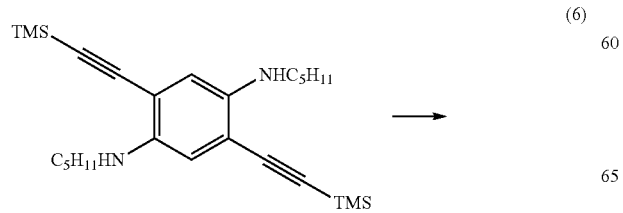

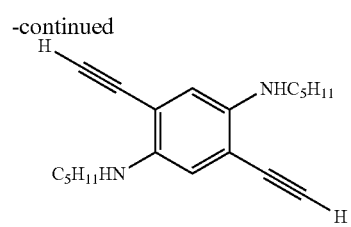

Example 7

In a pressure tube, to a solution of (6) (contaminated small amount of (7)) (about 100 mg of (6) & (7)) in DMSO (3 mL), is added 110 mg of crushed KOH. The reaction is stirred at 120° C. overnight to convert all (6) into (7). The reaction is brought to room temperature and the reaction mixture is extracted through ethyl acetate-water partitioning. Ethyl acetate is dried over MgSO$_4$ and evaporated under reduced pressure (MS found=MS calculated=296).

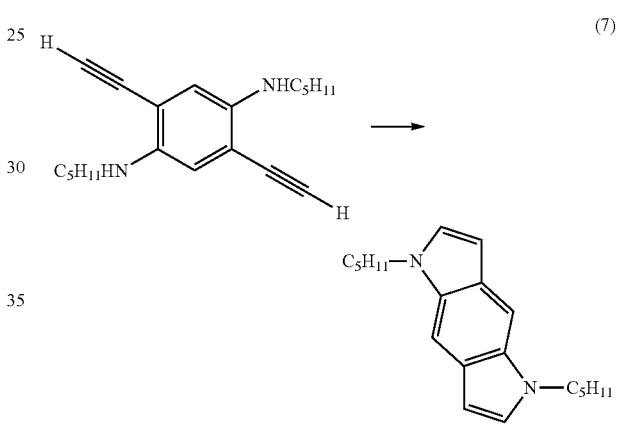

Example 8

The addition of non-hydrogen R-groups to the nitrogen on the pyrrole group, for example, a commercially available, unmodified diindole, can be done via use of a base such as t-BuOK in DMSO with subsequent reaction with an alkyl bromide:

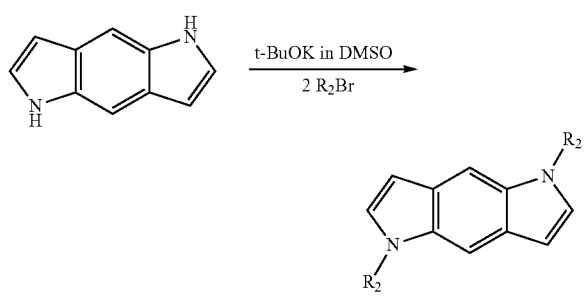

This reaction is based on work shown in references 34 New J. Chem. 1243 (2010) and 213 Macro. Chem. Phys. 425 (2012), herein incorporated by reference in their entireties.

Example 9

The compound formed in Example 8 can be reacted with N-butylsuccinimide to form the brominated diindole:

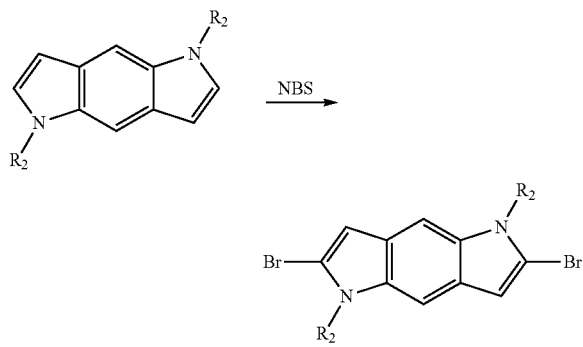

based on the teaching shown in PCT Publ. No. 2011/146308 (2011), herein incorporated by reference.

Example 10

The compound formed in Example can be reacted with n-BuLi in THF or hexane and then a tin complex for form the ditin diindole:

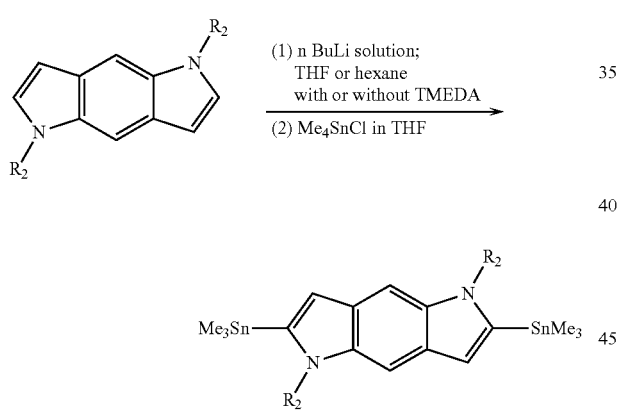

based on the teaching shown in U.S. Pat. No. 8,278,346, herein incorporated by reference.

What is claimed is:

1. A polymer comprising at least one moiety of formula:

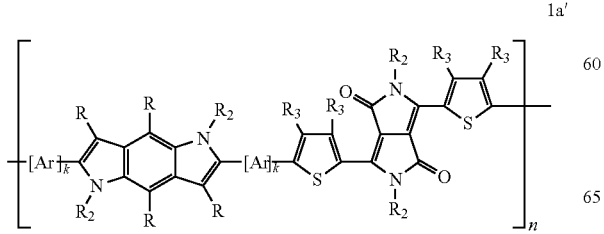

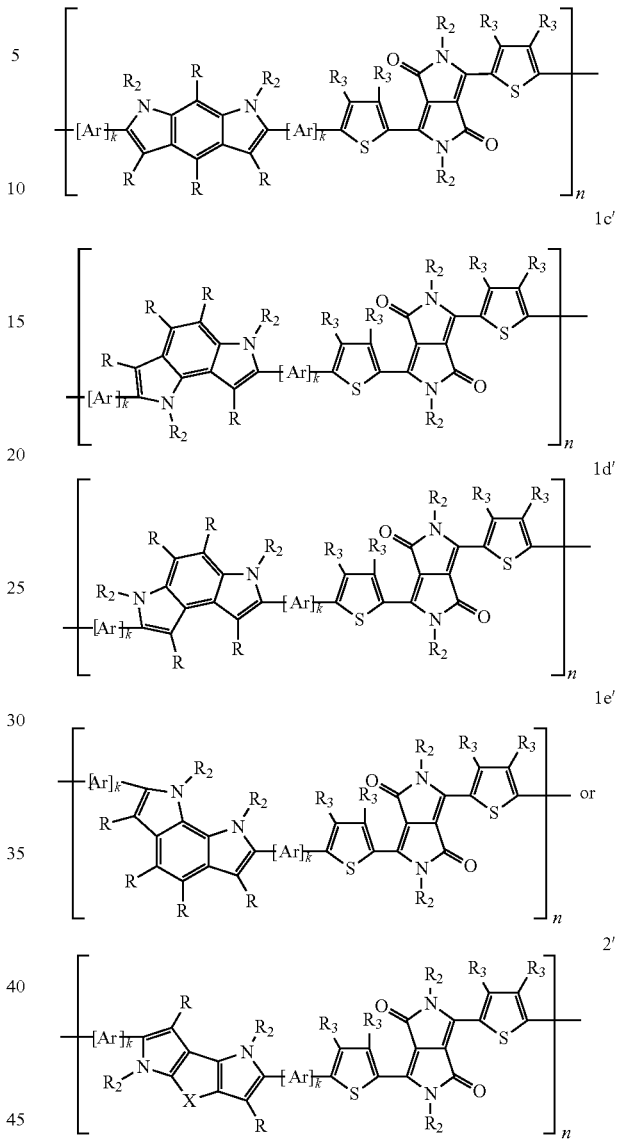

wherein n is an integer greater than zero; Ar is an optionally substituted aromatic or heteroaromatic group or conjugated group; k is an integer from 0 to 5 with the proviso that when k is 0, the structure results in a direct bond between the thiophene and pyrrole group; each X is independently $NR_1$, $PR_1$, $AsR_1$, Sb, O, S, Te, or Se, with the proviso that due to conjugation, X may be bonded to one or more additional $R_1$; and each R, $R_1$, $R_2$, and $R_3$ is independently H, halo, optionally substituted $C_1$-$C_{40}$ alkyl, optionally substituted aralkyl, alkoxy, alkylthio, optionally substituted $C_2$-$C_{40}$ alkenyl, optionally substituted $C_2$-$C_{40}$ alkynyl, aminocarbonyl, acylamino, acyloxy, optionally substituted aryl, aryloxy, optionally substituted amino, carboxyalkyl, optionally substituted cycloalkyl, optionally substituted cycloalkenyl, acyl, optionally substituted heteroaryl, optionally substituted heteroaralkyl, heteroaryloxy, optionally substituted heterocyclyl, thiol, alkylthio, heteroarylthiol, optionally substituted sulfoxide, or optionally substituted sulfone.

2. The polymer of claim 1, wherein n is an integer from 1 to 500.

3. The polymer of claim 2, wherein n is an integer from 3 to 20.

4. The polymer of claim 1, wherein the compound comprises structure 1a' or 1b'.

5. The polymer of claim 1, wherein the compound comprises structure 1c', 1d', or 1e'.

6. The polymer of claim 1, wherein the compound comprises structure 2'.

7. The polymer of claim 1, wherein k is from 0-3.

8. The polymer of claim 7, wherein k is 0.

9. The polymer of claim 1, wherein Ar is an optionally substituted aryl or heteroaryl.

10. The polymer of claim 9, wherein Ar is a thiophene or fused thiophene.

11. The polymer of claim 10, wherein the thiophene or fused thiophene is bonded to compound via the α positions and optionally substituted with one or more $C_1$-$C_{20}$ alkyl groups at the β positions.

12. The polymer of claim 1, wherein X is N, S, or O.

13. The polymer of claim 1, wherein X is N and Ar is an optionally substituted aryl or heteroaryl.

14. The polymer of claim 1, wherein each $R_1$ and $R_3$ are independently H, optionally substituted alkyl, halo, optionally substituted alkoxy, optionally substituted alkylthiol, or optionally substituted alkenyl.

15. The polymer of claim 14, wherein each R and $R_2$ are independently H, optionally substituted alkyl, halo, or optionally substituted alkoxy.

16. A method of making the polymer of claim 1, the method comprising reacting one or more compounds of formula:

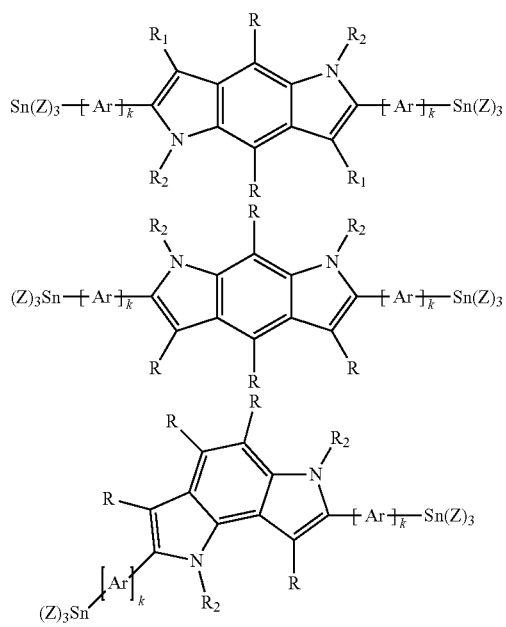

with one or more compounds of structure:

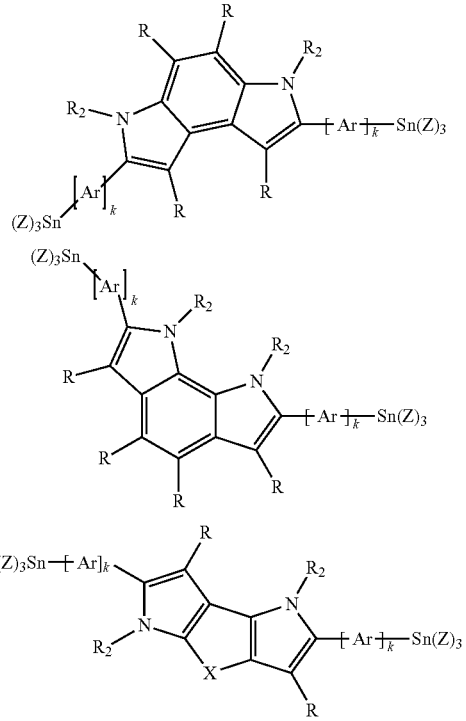

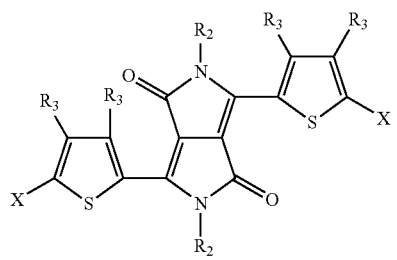

where X is halo and Z is H or an optionally substituted alkyl.

17. The method of claim 16, wherein k is from 0-3.

18. The method of claim 16, wherein Ar is an optionally substituted aryl or heteroaryl.

19. The method of claim 16, wherein X is N, S, or O.

20. The method of claim 1, wherein each $R_1$ and $R_3$ are independently H, optionally substituted alkyl, halo, optionally substituted alkoxy, optionally substituted alkylthiol, or optionally substituted alkenyl.

* * * * *